(12) United States Patent
Manyam

(10) Patent No.: US 11,429,086 B1
(45) Date of Patent: Aug. 30, 2022

(54) MODIFYING FUNCTIONS OF COMPUTING DEVICES BASED ON ENVIRONMENT

(71) Applicant: Amazon Technologies, Inc., Seattle, WA (US)

(72) Inventor: Ohil Krishnamurthy Manyam, Bellevue, WA (US)

(73) Assignee: Amazon Technologies, Inc., Seattle, WA (US)

( * ) Notice: Subject to any disclaimer, the term of this patent is extended or adjusted under 35 U.S.C. 154(b) by 115 days.

(21) Appl. No.: 15/994,963

(22) Filed: May 31, 2018

(51) Int. Cl.
*G05B 19/416* (2006.01)
*G01P 13/00* (2006.01)
*G01P 15/08* (2006.01)

(52) U.S. Cl.
CPC ............ *G05B 19/416* (2013.01); *G01P 13/00* (2013.01); *G01P 15/0802* (2013.01); *G05B 2219/42064* (2013.01)

(58) Field of Classification Search
CPC ... G05B 19/416; G01P 13/00; H04N 5/23218; H04N 1/2112; H04N 1/2129; H04N 1/32128; H04N 1/32101; H04N 2201/3201; H04N 2201/3253; H04N 2201/3254
See application file for complete search history.

(56) References Cited

U.S. PATENT DOCUMENTS

| | | | |
|---|---|---|---|
| 9,674,290 B1 | 6/2017 | Rincon et al. | |
| 9,824,490 B1 | 11/2017 | Côté et al. | |
| 2003/0229900 A1 | 12/2003 | Reisman | |
| 2004/0189675 A1 | 9/2004 | Pretlove et al. | |
| 2007/0162942 A1* | 7/2007 | Hamynen | G06F 3/011 725/105 |
| 2008/0101456 A1 | 5/2008 | Ridge et al. | |
| 2009/0015702 A1* | 1/2009 | Garcia Alonso | H04N 5/232939 348/333.02 |
| 2010/0088735 A1 | 4/2010 | Sadja et al. | |
| 2012/0092515 A1* | 4/2012 | Yim | H04N 5/23222 348/222.1 |
| 2013/0083003 A1 | 4/2013 | Perez et al. | |
| 2014/0100996 A1 | 4/2014 | Klein et al. | |
| 2015/0127486 A1 | 5/2015 | Advani | |

(Continued)

OTHER PUBLICATIONS

Editor, "uZoom Launches LiveShopCast to Power Live Video Sales", Home Business Magazine, Aug. 30, 2017, https://homebusinessmag.com/businesses/ecommerce/uzoom-launches-liveshopcast-power-live-video-sales/, pp. 1-4.

(Continued)

*Primary Examiner* — Nicholas G Giles
(74) *Attorney, Agent, or Firm* — Athorus, PLLC

(57) ABSTRACT

Systems and methods to modify functions of computing devices based on movements and/or locations of users of such computing devices may include various types of sensors, such as movement sensors, imaging sensors, and location sensors. The sensor data may be processed by various algorithms to determine either or both of movement and location of the user within an environment. Then, based at least on the determined movement or location of the user, a particular function level may be selected for the computing device to ensure safety and environmental awareness of the user. In addition, one or more functions of the computing device may be modified, enabled, disabled, automated, alerted, or otherwise changed based on the selected function level.

19 Claims, 10 Drawing Sheets

(56) References Cited

U.S. PATENT DOCUMENTS

| | | |
|---|---|---|
| 2015/0206542 A1 | 7/2015 | Gilson |
| 2015/0346722 A1 | 12/2015 | Herz et al. |
| 2016/0103437 A1 | 4/2016 | Alfredsson et al. |
| 2016/0142626 A1* | 5/2016 | Bostick .................. G06F 16/29 348/207.11 |
| 2016/0277802 A1 | 9/2016 | Bernstein et al. |
| 2016/0349509 A1 | 12/2016 | Lanier et al. |
| 2017/0041557 A1 | 2/2017 | Urich et al. |
| 2017/0061693 A1 | 3/2017 | Kohler et al. |
| 2017/0064154 A1 | 3/2017 | Tseng et al. |
| 2017/0124713 A1 | 5/2017 | Jurgenson et al. |
| 2017/0155725 A1 | 6/2017 | Rincon et al. |
| 2018/0115706 A1 | 4/2018 | Kang et al. |

OTHER PUBLICATIONS

Google Glass—Wikipedia, https://en.wikipedia.org/wiki/Google_Glass, downloaded from internet on Aug. 7, 2017, pp. 1-14.

Google Goggles—Wikipedia, https://en.wikipedia.org/wiki/Google_Goggles, downloaded from internet on Aug. 7, 2017, pp. 1-3.

Guven and Feiner, "Interaction Techniques for Exploring Historic Sites Through Situated Media," Proc. 3DUI '06 (Symposium on 3D User Interfaces), Alexandria, VA, Mar. 25-26, 2006, pp. 1-10.

Karsch, K., Golparvar-Fard, M., Forsyth, D. 2014 ConstructAide: Analyzing and Visualizing Construction Sites through Photographs and Building Models. ACM Trans. Graph. 33, 6, Article 176 (Nov. 2014), 11 pages.

Kinect—Wikipedia, https://en.wikipedia.org/wiki/Kinect, downloaded from internet on Aug. 7, 2017, pp. 1-15.

Microsoft HoloLens—Wikipedia, https://en.wikipedia.org/wiki/Microsoft_HoloLens, downloaded from internet on Aug. 7, 2017, pp. 1-8.

Samsung Gear VR—Wikipedia, https://en.wikipedia.org/wiki/Samsung_Gear_VR, downloaded from internet on Aug. 7, 2017, pp. 1-5.

URL: https://www.youvisit.com/ (Web Archive version dated Sep. 27, 2016, URL: https://web.archive.org/web/20160927064242/https://www.youvisit.com:80/), 7 pages.

Vlahakis et al., "Archeoguide: An Augmented Reality Guide for Archaeological Sites", IEEE Computer Graphics and Applications, Sep./Oct. 2002, pp. 52-60.

\* cited by examiner

MODIFYING FUNCTIONS OF COMPUTING DEVICES BASED ON ENVIRONMENT

BACKGROUND

Our world and universe is full of wonderful places, history, and natural wonders that people enjoy learning about and experiencing. People even plan special vacations, save money, and take time off from work to physically travel from their home location to a destination, often just to learn about and experience that destination location. However, physically visiting different locations is often cost and/or time prohibitive for many people. Others experience and learn about different places in the world by reading about those places, watching videos, and/or watching live presentations about those locations. However, those types of experiences require that the individual be a passive observer, watching and learning based on the information that is provided. Accordingly, there is a need for guided experiences provided via remote guides in which individuals may actively participate, and also during which the safety and local awareness of such remote guides may be ensured.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

Figure 1:
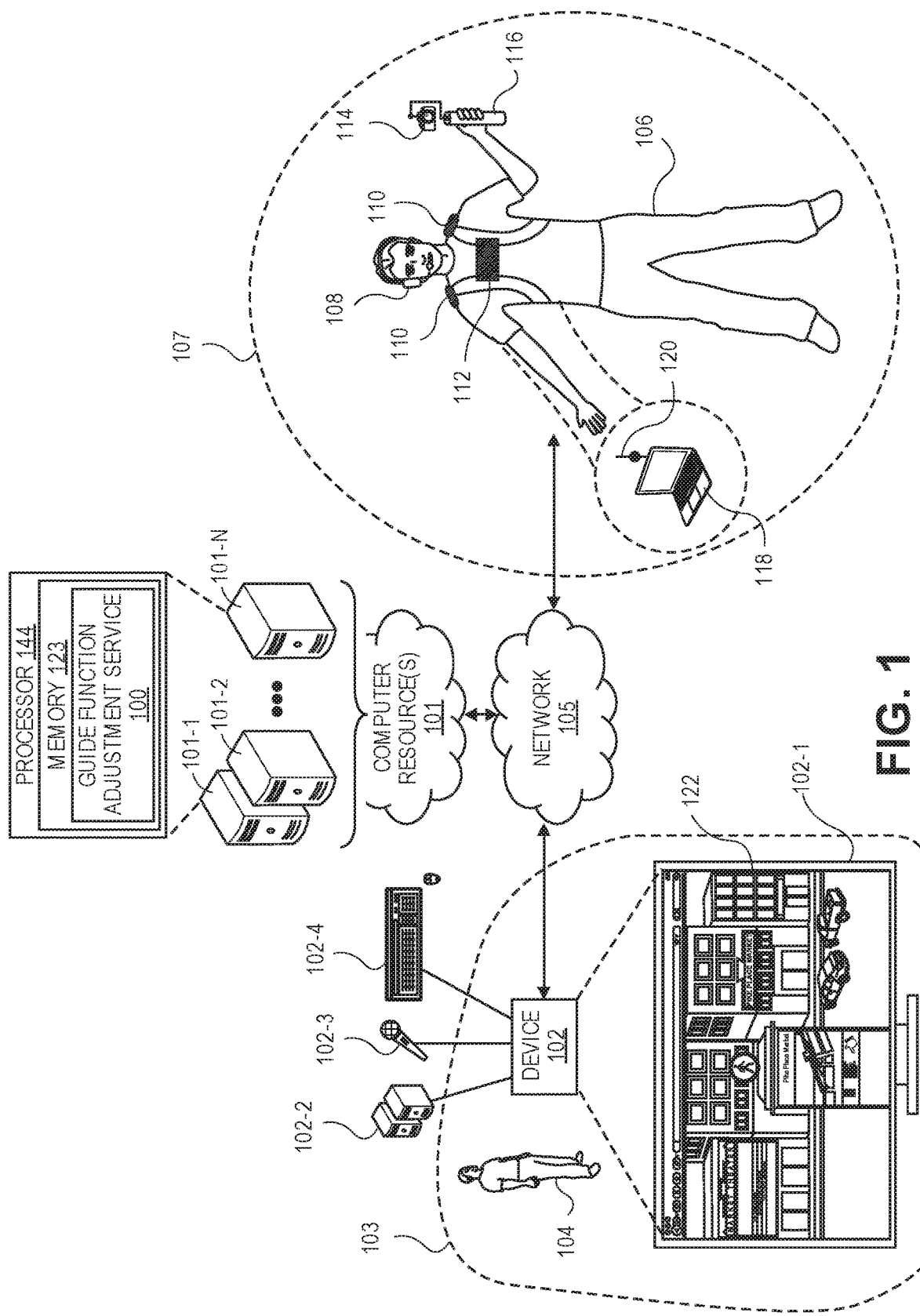
FIG. 1 is a schematic diagram of an example environment via which remote guided experiences may be presented to a user, according to an implementation.

While implementations are described herein by way of example, those skilled in the art will recognize that the implementations are not limited to the examples or drawings described. It should be understood that the drawings and detailed description thereto are not intended to limit implementations to the particular form disclosed but, on the contrary, the intention is to cover all modifications, equivalents and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

DETAILED DESCRIPTION

Systems and methods described herein relate to ensuring safety and environmental awareness of guides who may be providing remote guided experiences to users via a guide device. For example, a movement of a guide may be detected to determine various types of movement or acceleration of the guide. In addition, a location of a guide may be detected to determine a current location of the guide. Further, based on the movement and/or the location of the guide, a function level for the guide device may be determined from a plurality of available function levels that are associated with different types of movements and/or locations of the guide. Moreover, based on the determined function level for the guide device, one or more functions may be modified to ensure safety and environmental awareness of the guide.

In example embodiments, a movement of a guide may be detected by various types of sensors, including acceleration sensors, imaging sensors, or environment sensors. For example, the acceleration sensors may detect various accelerations experienced by the guide, and such detected accelerations may be compared or correlated with known accelerations associated with various types of movement. In addition, the imaging sensors may capture optical flow data and/or imaging data of surroundings, and the optical flow or imaging data may be processed to determine various types of movement of the guide. Further, the environment sensors may detect changes in wind speed, changes in altitude, or other environmental changes, and such data may be processed to determine various types of movement of the guide.

In additional example embodiments, a location of a guide may be detected by various types of sensors, including location sensors, imaging sensors, or environment sensors. For example, the location sensors may receive location data from one or more location networks, such as global positioning systems (GPS), and a current location of the guide may be determined based on such location data. In addition, the imaging sensors may capture imaging data of surroundings, and one or more recognized objects within such imaging data may be compared with known objects to determine a current location of the guide. Further, the environment sensors may detect an altitude or other environmental aspects associated with the guide, and such data may be processed to determine a current location of the guide.

In further example embodiments, based on a movement and/or a location of a guide, one or more machine learning models or other processing algorithms, models, or tools may determine a function level for the guide device. The function level may be determined from a plurality of function levels that are each associated with a respective movement and/or location of a guide. For example, if the movement and/or location of the guide indicates that the guide is traversing uneven terrain, then a first function level may be determined for the guide device. If the movement and/or location of the guide indicates that the guide is going up or down stairs, then a second function level may be determined for the guide device. If the movement and/or location of the guide indicates that the guide is currently in a congested location, then a third function level may be determined for the guide device. In addition, if the movement and/or location of the guide indicates that the guide is walking at a steady pace, then a fourth function level may be determined for the guide device. If the movement and/or location of the guide indicates that the guide is sitting, then a fifth function level may be determined for the guide device. If the movement and/or location of the guide indicates that the guide is currently inside a museum, library or cafe, then a sixth function level may be determined for the guide device.

In additional example embodiments, based on the determined function level for the guide device, one or more functions of the guide device may be modified. The one or more functions may be modified from a plurality of available functions of the guide device, including transmission of video and/or audio data, control of imaging devices, various selectable user interface elements, menu options, purchase workflows, chat or other communications, or other functions. For example, the one or more functions may be enabled, disabled, suppressed, presented on a user interface, removed from the user interface, configured for manual control, configured for automatic control, or otherwise modified. In addition, one or more notifications related to one or more functions may also be presented to the guide via the guide device. Further, one or more options to override or change the function level, and associated available functions, of the guide device may also be presented to the guide, such that the guide may manually override or change the determined function level as desired.

By the systems and methods described herein, safety and environmental awareness of guides who may be providing remote guided experiences to users may be ensured. In various example embodiments, one or more functions of the guide device may be automatically adjusted based on a current movement and/or location of a guide, while also allowing flexibility to the guide to manually override or change such adjustments as desired and in order to not detract from the guided experiences provided to users.

FIG. 1 is a schematic diagram of an example environment via which remote guided experiences may be presented to a user, according to an implementation. As illustrated, the guide 106 is located at a destination location 107, which may be any location in the world, or as our travel capabilities continue to expand, any location in the universe. The guide carries and operates a guide device. The guide device includes at least one imaging component 114, such as a digital camera, a video camera, or other form of imaging component, that may be controlled by commands sent from a user device 102 and/or controlled by the guide 106. In some implementations, the imaging component 114 may be an infrared camera, a thermal imaging camera, and/or other form of imaging component. The user 104 and the user device 102 are positioned at any location, such as a user location 103 that is separate and distinct from the destination location 107. In some implementations, the imaging component 114 may be mounted to a gimbal 116, such as a two or three-axis gimbal that is held or otherwise mounted to the guide. In other implementations, the imaging component 114 may be mounted to the guide. The imaging component 114 captures images of the destination location in the form of video data and transmits those images over a network 105 to the user device 102 and/or to the remote computing resources 101 for processing.

The guide device may also include one or more microphones 110 for receiving audio input from sounds within the destination location, and one or more speakers 112 for outputting sound into the environment. For example, the user 104, using a microphone at the user device 102 may provide audio input (e.g., speech) that is transmitted via the network 105 to the guide device and output through the one or more speakers 112 of the guide device.

The guide device may also include a headset 108 that enables audio communication directly between the user 104 and the guide 106. As illustrated, the headset 108 may also include a speaker (or earphone) that is used to output audio to the guide 106, and a microphone that is used by the guide to communicate directly with the user 104. The microphone(s) 110 and/or the microphone of the headset 108 may be configured to capture sounds (e.g., utterances) from a user speaking, other sounds of the destination location, and/or sounds (e.g., utterances) of the guide. The audio signal/data may then be sent over the network 105 to the user device 102 and output through a speaker of the user device.

The guide device may also include a computing component 118, a transmitter/receiver, and an antenna 120. The antenna 120 enables wireless transmission (transmitting/receiving) between the guide device, the remote computing resources 101 and the user device 102. Additional details of an example guide device are discussed further herein with respect to FIG. 9.

Transmission between the guide device, the user device 102, and/or the computing resources 101 may be via a network 105. The network 105 may include wired technologies (e.g., wires, USB, fiber optic cable, etc.), wireless technologies (e.g., RF, cellular, satellite, Bluetooth, etc.), and/or other connection technologies. The network 105 carries data between the guide devices, the remote computing resources 101, and one or more user devices 102. For example, the network 105 may carry video data and/or audio data from the guide device to the user device 102 so that the video data and/or audio data can be presented by the user device 102 to the user 104 in near real-time. For example, the presentation 122 may be video data generated from the imaging component 114 of the guide device. The presentation may be displayed on a display 102-1 of the user device 102, projected by a camera or projector of the user device, output audibly using speakers 102-2 of the user device 102, etc.

In some implementations, video data and/or audio data from a guide device may be transmitted to multiple user devices. For example, video data and/or audio data from the guide device may be transmitted over the network 105 to the computer resources 101 and the computer resources may send the video data and/or audio data to the user device 102 and one or more other user devices.

In example embodiments, the video data generated from the imaging component 114 of the guide device may also be presented to the guide via a display associated with the imaging component 114, the computing component 118, a wearable device or headset, or any other component of the guide device, or via a separate display component of the guide device. In addition, as further described herein, one or more functions, user interface elements, and/or notifications may be presented to the guide via such a display, e.g., overlaid or presented together with the video data from the imaging component 114.

As illustrated, the remote computing resources 101 may include one or more servers, such as servers 101-1, 101-2, . . . , 101-N. These servers 101-1-101-N may be arranged in any number of ways, such as server farms, stacks, and the like that are commonly used in data centers. Furthermore, the servers 101-1-101-N may include one or more processors 144 and memory 123, which may store a guide function adjustment service 100 that executes one or more of the processes or features discussed herein.

For example, the guide function adjustment service 100 may receive data from various sensors associated with a movement and/or a location of the guide and guide device, may process the received data to determine a movement and/or current location of the guide and guide device, may identify a function level for the guide device based at least in part on the determined movement and/or current location, and/or may modify one or more functions available to the guide via the guide device based at least in part on the determined function level.

The user device 102 may be any type of device that is capable of receiving and presenting video data and/or audio data to a user 104 and that is capable of transmitting control instructions to the guide device to control the imaging component 114 of the guide device. For example, the user device 102 may be a cellular phone, smart phone, desktop, laptop, and/or any other form of computing device. The user device 104 may be configured to include, among other components, a display 102-1, such as a touch-based display, one or more speakers 102-2, one or more microphones 102-3, and/or one or more interface components such as a mouse or keyboard 102-4. The speakers 102-2 output sounds transmitted from the guide device to the user device 102. The microphone(s) 102-3 capture sounds (e.g., utterances) from a user 104 speaking. Those sounds are converted into audio signals, transmitted over the network 105 to the guide device and output through the guide's 106 headset 108 and/or the speakers 112. The interface components, such as the mouse and keyboard 102-4, may be used to control the orientation of the imaging component 114 of the guide device. For example, the user 104 may utilize an interface component to input direction or orientation commands that are transmitted over the network 105 to the guide device and used to control or alter the position or orientation of the imaging component 114.

As video data is captured by the imaging component 114 of the guide device, the video data is processed, transmitted, and/or displayed via a display 102-1 of the user device, via a display associated with the guide device, and/or via other displays associated with the example environment. As discussed further herein, processing of the video may be done by the computing component 118 of the guide device, by the remote computing resources 101, by the user device 102, and/or by a combination of two or more of the computing component 118 of the guide device, the remote computing resources 101, and the user device 102.

In example embodiments, the guide device may also include one or more sensors to detect a movement and/or location of the guide and guide device. As further described herein, the one or more sensors may include various types of sensors, such as movement or acceleration sensors, a compass or magnetic sensors, imaging sensors, location sensors, environment sensors, audio sensors, or other types of sensors. The one or more sensors may be associated with various components of the guide device, such as the imaging component 114, the gimbal 116, the computing component 118, a backpack, bag, or wearable component or device that may comprise or house one or more components of the guide device, or any other component of the guide device. Data from the one or more sensors may be processed and used to determine a function level for the guide device, as well as to modify one or more functions thereof. Processing of the data from the one or more sensors may be done by the computing component 118 of the guide device, by the guide function adjustment service 100 of the remote computing resources 101, or by a combination thereof.

Figure 2:
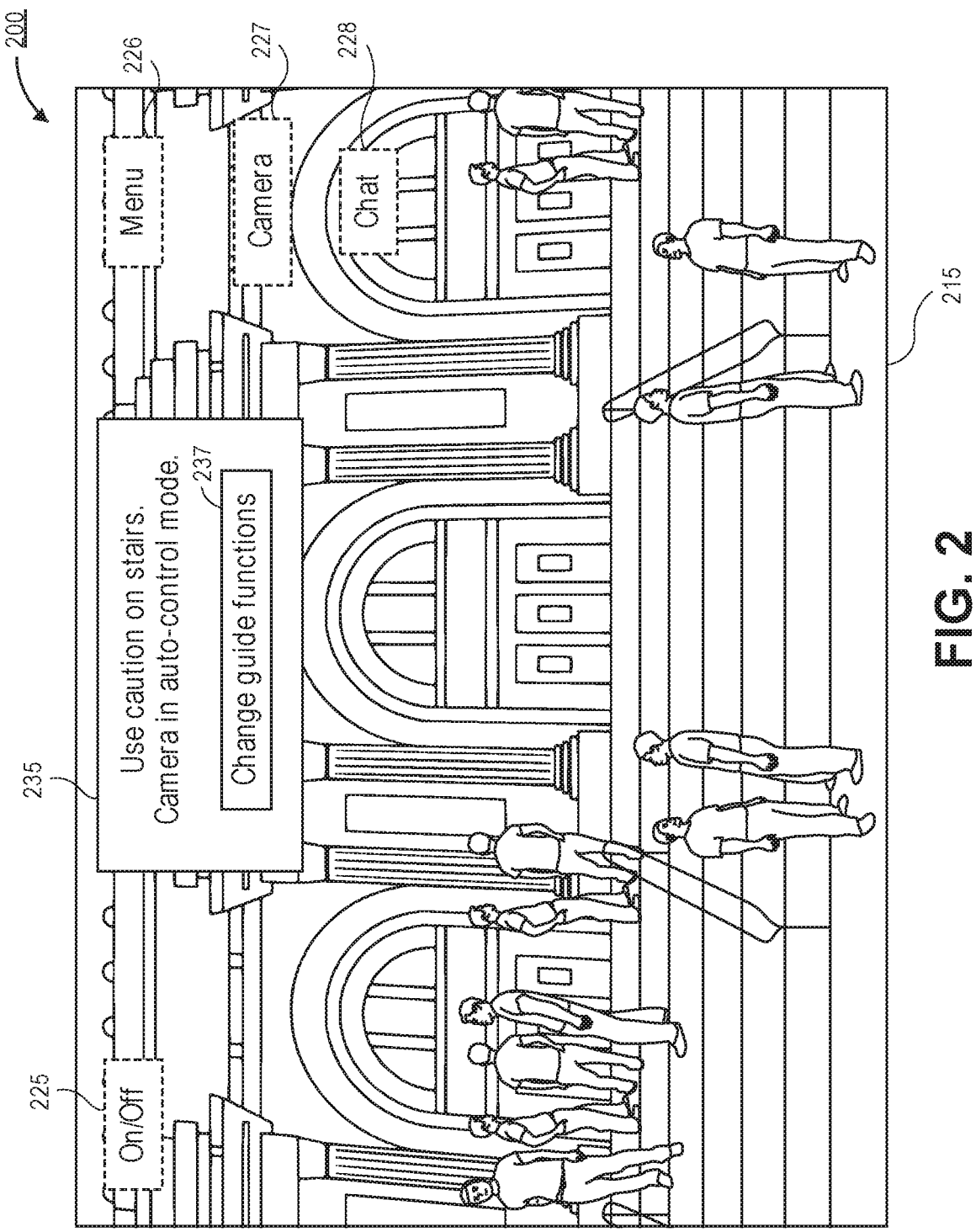
FIG. 2 is a schematic diagram of example video data presented by a guide device, according to an implementation.

FIG. 2 is a schematic diagram of example video data 200 presented by a guide device, according to an implementation.

As shown in FIG. 2, a guide may be located at an entrance to a museum, e.g., the Metropolitan Museum of Art, and may be ascending or descending stairs at the entrance. An imaging component of the guide device may capture imaging data 215 of the current location, and the imaging data 215 may be presented to the guide via a display associated with the guide device. In addition, one or more sensors associated with the guide device may detect aspects related to movement and/or location of the guide and guide device as the guide ascends/descends stairs at the museum entrance.

In example embodiments, one or more movement sensors, such as inertial measurement units, accelerometers, or gyroscopes, may detect aspects of the movement of the guide. Movement data received from the movement sensors may be processed to determine that the guide is walking and ascending/descending stairs. In addition, one or more imaging sensors, including the imaging component, may capture imaging data of the location of the guide. Imaging data received from the imaging sensors may be processed to identify motion of objects in the imaging data, and determine that the guide is walking and ascending/descending stairs. Further, one or more environment sensors, such as a wind sensor or audio sensors, may detect aspects of the environment around the guide. Wind data and/or audio data received from the environment sensors may be processed to determine that the guide is walking and ascending/descending stairs.

In other example embodiments, one or more location sensors, such as GPS sensors, indoor positioning system sensors, cellular signal sensors, other network signal sensors, or other location sensors, may receive location data related to the guide. Location data received from the location sensors may be processed to determine a current location of the guide. In addition, one or more imaging sensors, including the imaging component, may capture imaging data of the location of the guide. Imaging data received from the imaging sensors may be processed to recognize one or more objects in the imaging data, and determine a current location of the guide based on stored information of known objects and their locations. Further, one or more environment sensors, such as a temperature sensor or weather sensor, may detect aspects of the environment around the guide. Temperature and weather data received from the environment sensors may be processed to determine a current location of the guide.

Moreover, although the data from various sensors is described herein individually, various combinations of data from the various sensors may be received and processed to more accurately and reliably determine movements and/or locations of guides and guide devices.

Based on the received and processed data from various sensors, it may be determined that the guide is ascending/descending stairs at the entrance of the Metropolitan Museum of Art. Then, a guide function level may be determined based at least in part on the determined movement (e.g., ascending/descending stairs) and location (e.g., entrance to the Met). The guide function level may be determined from a plurality of guide function levels, e.g., ranging from full functionality available via a guide device (e.g., including two-way communication and video/audio data transmission, fully enabled user interface elements, and full manual control of components of the guide device) to very limited functionality available via a guide device (e.g., including no communication and only video data transmission, fully disabled user interface elements, and full automatic control of components of the guide device). For example, the guide function level may be determined based on prior guide function levels used for the same determined movement and location. In addition, the guide function level may be determined based on similar prior guide function levels used for similar determined movements and locations (e.g., ascending/descending stairs at different museums, ascending/descending stairs in other environments, etc.).

Then, based on the determined guide function level, one or more modifications may be made to the functions available to the guide via the guide device. Various functions that may generally be available via the guide device may include two-way video data transmission, two-way audio data transmission, two-way audio communication, two-way chat communication, full manual control of components of the guide device, full manual control of the imaging component, fully enabled user interface elements, completion of purchase workflows, triggering of digital assets or supplemental content, or other functions. Modifications to the various functions may include enabling, disabling, suppressing, or otherwise changing the availability of one or more functions. In addition, modifications to the various functions may include switching between manual, semi-automatic, or automatic control of one or more functions or components of the guide device. Further, modifications to the various functions may also include notifications related to one or more functions to inform the guide of current adjustments to the guide device. Moreover, the notifications may comprise various types of notifications, including visual, audio, haptic, or other types of notifications or feedback.

For example, as shown in FIG. 2, user interface elements 225, 226, 227, 228 may be disabled, e.g., grayed out, so as to encourage the guide to focus on ascending/descending stairs. In addition, one or more notifications 235 to alert the guide may be presented via the display, further reinforcing that the guide should focus on ascending/descending stairs. Further, the notifications 235 may also provide information related to modified functions of one or more components of the guide device, e.g., automatic control of the camera. Further, an override option 237 may also be presented via the display to the guide such that the guide may manually change one or more functions of the guide device as desired. In this manner, a guide may be allowed to override or selectively change one or more available functions to continue to provide a valuable experience to the user. In addition, such overrides or selections by guides may be processed over time to refine the processing algorithms that determine guide function levels and associated function modifications as they relate to particular movements and/or locations of guides and guide devices.

Figure 3:
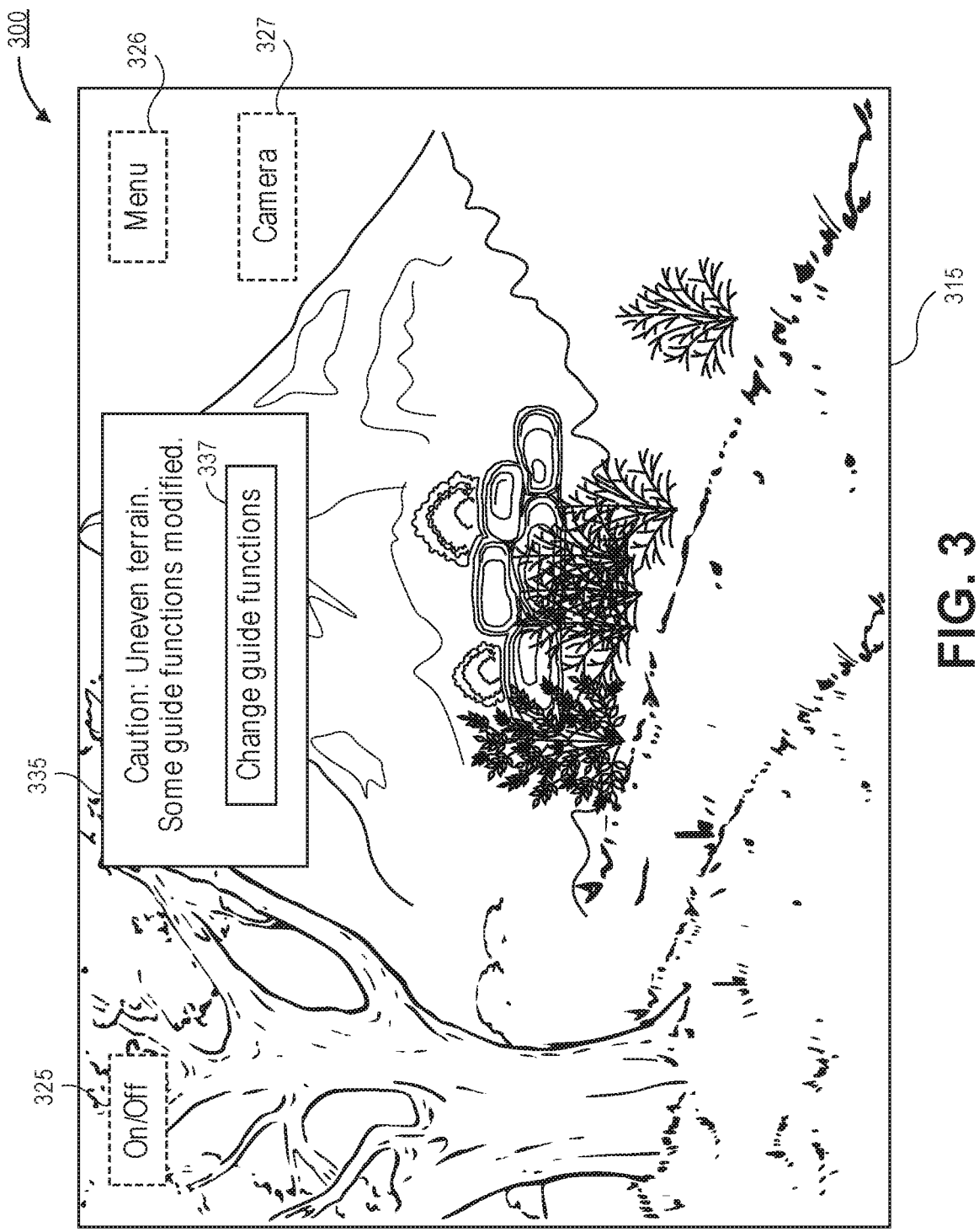
FIG. 3 is a schematic diagram of another example video data presented by a guide device, according to an implementation.

FIG. 3 is a schematic diagram of another example video data 300 presented by a guide device, according to an implementation.

As shown in FIG. 3, a guide may be located on a trail within a park, e.g., a walking trail within Central Park, and may be walking on uneven terrain in a wooded environment. An imaging component of the guide device may capture imaging data 315 of the current location, and the imaging data 315 may be presented to the guide via a display associated with the guide device. In addition, one or more sensors associated with the guide device may detect aspects related to movement and/or location of the guide and guide device as the guide walks on the uneven terrain.

In example embodiments, one or more movement sensors, such as inertial measurement units, accelerometers, or gyroscopes, may detect aspects of the movement of the guide. Movement data received from the movement sensors may be processed to determine that the guide is walking on uneven terrain. In addition, one or more imaging sensors, including the imaging component, may capture imaging data of the location of the guide. Imaging data received from the imaging sensors may be processed to identify motion of objects in the imaging data, and determine that the guide is walking on uneven terrain in a wooded environment. Further, one or more environment sensors, such as a wind sensor, altitude sensors, or audio sensors, may detect aspects of the environment around the guide. Wind, altitude, and/or audio data received from the environment sensors may be processed to determine that the guide is walking on uneven terrain in a wooded environment.

In other example embodiments, one or more location sensors, such as GPS sensors, indoor positioning system sensors, cellular signal sensors, other network signal sensors, or other location sensors, may receive location data related to the guide. Location data received from the location sensors may be processed to determine a current location of the guide. In addition, one or more imaging sensors, including the imaging component, may capture imaging data of the location of the guide. Imaging data received from the imaging sensors may be processed to recognize one or more objects in the imaging data, and determine a current location of the guide based on stored information of known objects and their locations. Further, one or more environment sensors, such as a temperature sensor, altitude sensor, or weather sensor, may detect aspects of the environment around the guide. Temperature, altitude, and weather data received from the environment sensors may be processed to determine a current location of the guide.

Moreover, although the data from various sensors is described herein individually, various combinations of data from the various sensors may be received and processed to more accurately and reliably determine movements and/or locations of guides and guide devices.

Based on the received and processed data from various sensors, it may be determined that the guide is walking on uneven terrain on a trail within Central Park. Then, a guide function level may be determined based at least in part on the determined movement (e.g., walking on uneven terrain) and location (e.g., wooded environment). The guide function level may be determined from a plurality of guide function levels, e.g., ranging from full functionality available via a guide device (e.g., including two-way communication and video/audio data transmission, fully enabled user interface elements, and full manual control of components of the guide device) to very limited functionality available via a guide device (e.g., including no communication and only video data transmission, fully disabled user interface elements, and full automatic control of components of the guide device). For example, the guide function level may be determined based on prior guide function levels used for the same determined movement and location. In addition, the guide function level may be determined based on similar prior guide function levels used for similar determined movements and locations (e.g., walking on uneven terrain at different parks in New York, hiking trails in other natural environments, etc.).

Then, based on the determined guide function level, one or more modifications may be made to the functions available to the guide via the guide device. Various functions that may generally be available via the guide device may include two-way video data transmission, two-way audio data transmission, two-way audio communication, two-way chat communication, full manual control of components of the guide device, full manual control of the imaging component, fully enabled user interface elements, completion of purchase workflows, triggering of digital assets or supplemental content, or other functions. Modifications to the various functions may include enabling, disabling, suppressing, or otherwise changing the availability of one or more functions. In addition, modifications to the various functions may include switching between manual, semi-automatic, or automatic control of one or more functions or components of the guide device. Further, modifications to the various functions may also include notifications related to one or more functions to inform the guide of current adjustments to the guide device. Moreover, the notifications may comprise various types of notifications, including visual, audio, haptic, or other types notifications or feedback.

For example, as shown in FIG. 3, user interface elements 325, 326, 327 may be disabled, e.g., grayed out, so as to encourage the guide to focus on walking the trail. In addition, one or more notifications 335 to alert the guide may be presented via the display, further reinforcing that the guide should focus on walking the trail. Further, the notifications 335 may also provide information related to modified functions of one or more components of the guide device. Further, an override option 337 may also be presented via the display to the guide such that the guide may manually change one or more functions of the guide device as desired. In this manner, a guide may be allowed to override or selectively change one or more available functions to continue to provide a valuable experience to the user. In addition, such overrides or selections by guides may be processed over time to refine the processing algorithms that determine guide function levels and associated function modifications as they relate to particular movements and/or locations of guides and guide devices.

Various other modifications to functions may also be performed in combination with those already described with respect to FIG. 3. For example, one or more digital assets or supplemental content related to the movement and/or location of the guide may be automatically triggered and provided to the user. In the context of FIG. 3, digital or supplemental content related to the particular walking trail in Central Park may be provided to the user. In addition, supplemental information related to the various flora along the walking trail may also be provided to the user. Moreover, one or more aspects of operation of the guide device may also be modified. For example, various sounds, noises, light, heat, or other aspects emitted by or associated with one or more components of the guide device may be softened, reduced, muted, or otherwise changed so as not to adversely affect the surroundings of the walking trail.

Figure 4:
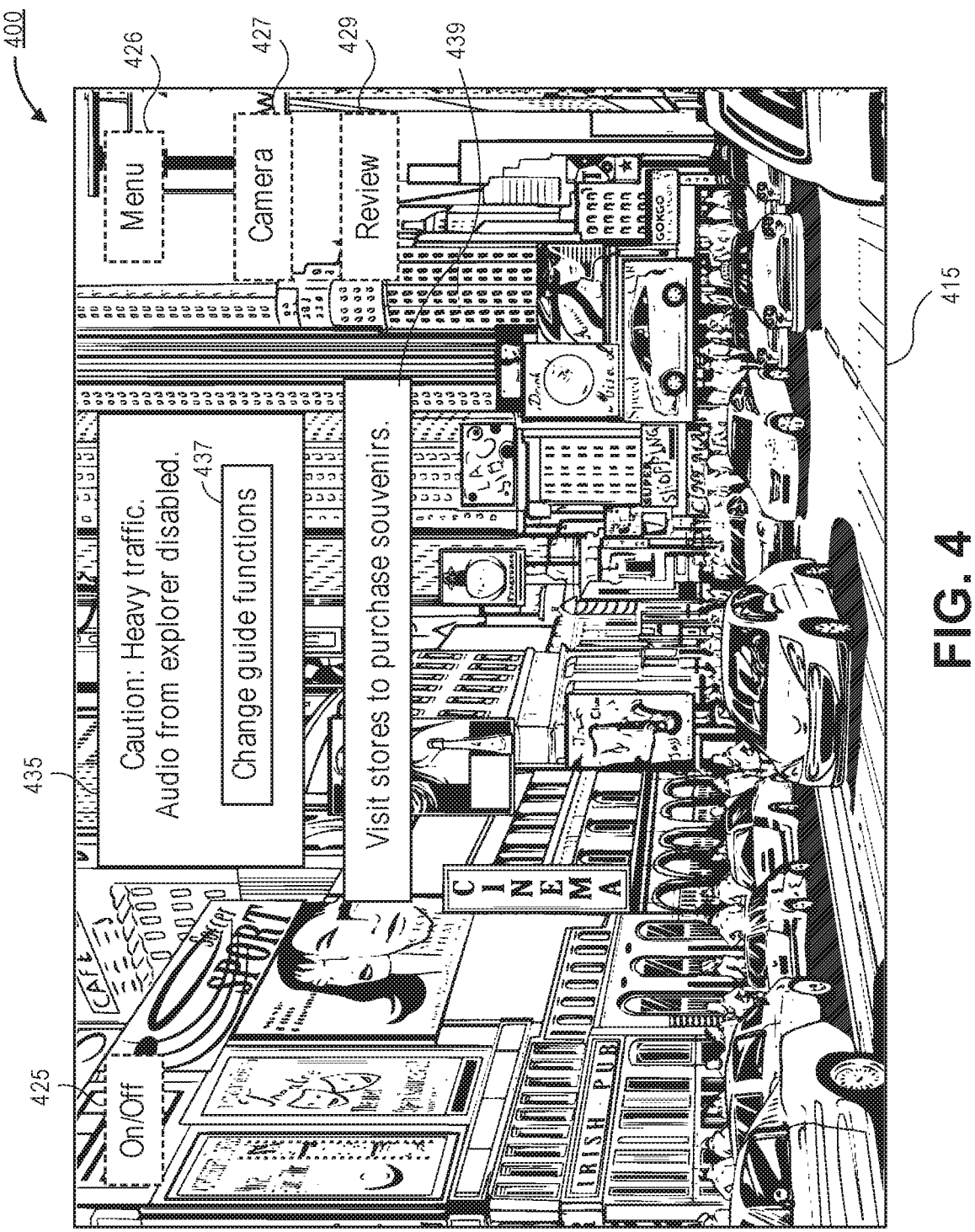
FIG. 4 is a schematic diagram of yet another example video data presented by a guide device, according to an implementation.

FIG. 4 is a schematic diagram of yet another example video data 400 presented by a guide device, according to an implementation.

As shown in FIG. 4, a guide may be located at a congested corner in an urban environment, e.g., Times Square, and may be crossing a crowded street full of cars and pedestrians. An imaging component of the guide device may capture imaging data 415 of the current location, and the imaging data 415 may be presented to the guide via a display associated with the guide device. In addition, one or more sensors associated with the guide device may detect aspects related to movement and/or location of the guide and guide device as the guide walks on the uneven terrain.

In example embodiments, one or more movement sensors, such as inertial measurement units, accelerometers, or gyroscopes, may detect aspects of the movement of the guide. Movement data received from the movement sensors may be processed to determine that the guide is walking on crowded city streets. In addition, one or more imaging sensors, including the imaging component, may capture imaging data of the location of the guide. Imaging data received from the imaging sensors may be processed to identify motion of objects in the imaging data, and determine that the guide is walking on crowded city streets. Further, one or more environment sensors, such as a wind sensor, altitude sensors, or audio sensors, may detect aspects of the environment around the guide. Wind, altitude, and/or audio data received from the environment sensors may be processed to determine that the guide is walking on crowded city streets.

In other example embodiments, one or more location sensors, such as GPS sensors, indoor positioning system sensors, cellular signal sensors, other network signal sensors, or other location sensors, may receive location data related to the guide. Location data received from the location sensors may be processed to determine a current location of the guide. In addition, one or more imaging sensors, including the imaging component, may capture imaging data of the location of the guide. Imaging data received from the imaging sensors may be processed to recognize one or more objects in the imaging data, and determine a current location of the guide based on stored information of known objects and their locations. Further, one or more environment sensors, such as a temperature sensor or weather sensor, may detect aspects of the environment around the guide. Temperature and weather data received from the environment sensors may be processed to determine a current location of the guide.

Moreover, although the data from various sensors is described herein individually, various combinations of data from the various sensors may be received and processed to more accurately and reliably determine movements and/or locations of guides and guide devices.

Based on the received and processed data from various sensors, it may be determined that the guide is crossing a crowded street in Times Square. Then, a guide function level may be determined based at least in part on the determined movement (e.g., walking on crowded city streets) and location (e.g., Times Square). The guide function level may be determined from a plurality of guide function levels, e.g., ranging from full functionality available via a guide device (e.g., including two-way communication and video/audio data transmission, fully enabled user interface elements, and full manual control of components of the guide device) to very limited functionality available via a guide device (e.g., including no communication and only video data transmission, fully disabled user interface elements, and full automatic control of components of the guide device). For example, the guide function level may be determined based on prior guide function levels used for the same determined movement and location. In addition, the guide function level may be determined based on similar prior guide function levels used for similar determined movements and locations (e.g., walking along other streets in New York, crossing streets near other tourist attractions, etc.).

Then, based on the determined guide function level, one or more modifications may be made to the functions available to the guide via the guide device. Various functions that may generally be available via the guide device may include two-way video data transmission, two-way audio data transmission, two-way audio communication, two-way chat communication, full manual control of components of the guide device, full manual control of the imaging component, fully enabled user interface elements, completion of purchase workflows, triggering of digital assets or supplemental content, or other functions. Modifications to the various functions may include enabling, disabling, suppressing, or otherwise changing the availability of one or more functions. In addition, modifications to the various functions may include switching between manual, semi-automatic, or automatic control of one or more functions or components of the guide device. Further, modifications to the various functions may also include notifications related to one or more functions to inform the guide of current adjustments to the guide device. Moreover, the notifications may comprise various types of notifications, including visual, audio, haptic, or other types notifications or feedback.

For example, as shown in FIG. 4, user interface elements 425, 426, 427, 429 may be disabled, e.g., grayed out, so as to encourage the guide to focus on crossing the crowded street. In addition, one or more notifications 435 to alert the guide may be presented via the display, further reinforcing that the guide should focus on crossing the crowded street. Further, the notifications 435 may also provide information related to modified functions of one or more components of the guide device, e.g., only one-way audio communication enabled from the guide to the user. Further, an override option 437 may also be presented via the display to the guide such that the guide may manually change one or more functions of the guide device as desired. In this manner, a guide may be allowed to override or selectively change one or more available functions to continue to provide a valuable experience to the user. In addition, such overrides or selections by guides may be processed over time to refine the processing algorithms that determine guide function levels and associated function modifications as they relate to particular movements and/or locations of guides and guide devices.

Various other modifications to functions may also be performed in combination with those already described with respect to FIG. 4. For example, one or more purchase opportunities may be made available as the guide visits one or more stores in the environment, and the guide may be instructed by an additional notification 439 to visit one or more stores to enable purchase workflows and other functions related to such purchase opportunities. That is, although such purchase workflows may be unavailable as the guide is crossing crowded city streets, the guide may be reminded of the availability of such purchase workflows responsive to pausing at one or more stores as part of the experience for the user. In addition, digital assets or supplemental content related to the movement and/or location of the guide may be automatically triggered and provided to the user. In the context of FIG. 4, digital or supplemental content related to Times Square, its history, events, or other information may be provided to the user. Moreover, one or more aspects of operation of the guide device may also be modified. For example, in noisy, bright, or crowded environments, various sounds, noises, light, or other aspects emitted by or associated with one or more components of the guide device may be sharpened, increased, emphasized, or otherwise changed so as to maintain coordination and communication between the guide, the guide device, and the user.

In further example embodiments, a display or other components of the user device associated with a user viewing the experience provided by the guide and guide device may also be modified in a manner corresponding to changes to guide function levels and functions. For example, one or more user interface elements presented to the user may be enabled, disabled, or otherwise modified. In addition, various options to control the imaging component, gimbal, or other components of the guide device may also be enabled, disabled, or otherwise modified. Further, various channels for communicating with the guide may be enabled, disabled, or otherwise modified. Moreover, one or more notifications may also be presented or provided to the user related to changes to guide functions based on movement and/or location of the guide device. Furthermore, options to manually override or change functions available to the user and/or the guide may also be presented to the user; however, such options may be limited in order to maintain safety and environmental awareness of the guide.

In example embodiments, one or more processing algorithms, models, or tools, including machine learning algorithms or models, image recognition algorithms or models, and other algorithms or models, may be used to process the data received from various sensors related to movement and/or location of the guide and guide device. In addition, one or more processing algorithms, models, or tools may be used to determine a guide function level based at least in part on the determined movement and/or location of the guide and guide device. Further, one or more processing algorithms, models, or tools may also be used to modify one or more functions of the guide device based at least in part on the determined guide function level.

In example embodiments, machine learning models or algorithms may comprise various types of machine learning algorithms, techniques, or models that may receive various data, e.g., data from various sensors, and/or data, results, or outputs from other processing algorithms, and process such received data in order to determine movements, locations, guide function levels, and/or function modifications associated with guides and guide devices. Example machine learning models may comprise artificial neural networks, deep neural networks, or any other machine learning algorithms, techniques, or models.

Machine learning models or tools, such as artificial neural networks, have been utilized to identify relations between respective elements of apparently unrelated sets of data. An artificial neural network is a parallel distributed computing processor comprised of individual units that may collectively learn and store experimental knowledge, and make such knowledge available for use in one or more applications. Such a network may simulate the non-linear mental performance of the many neurons of the human brain in multiple layers by acquiring knowledge from an environment through one or more flexible learning processes, determining the strengths of the respective connections between such neurons, and utilizing such strengths when storing acquired knowledge. Like the human brain, an artificial neural network may use any number of neurons in any number of layers, including an input layer, an output layer, and one or more intervening hidden layers. In view of their versatility, and their inherent mimicking of the human brain, machine learning tools including not only artificial neural networks but also nearest neighbor methods or analyses, factorization methods or techniques, K-means clustering analyses or techniques, similarity measures such as log likelihood similarities or cosine similarities, latent Dirichlet allocations or other topic models, or latent semantic analyses, have been utilized in various data processing applications.

Artificial neural networks may be trained to map inputted data to desired outputs by adjusting the strengths of the connections between one or more neurons, which are sometimes called synaptic weights. An artificial neural network may have any number of layers, including an input layer, an output layer, and any number of intervening hidden layers. Each of the neurons in a layer within a neural network may receive an input and generate an output in accordance with an activation or energy function, with parameters corresponding to the various strengths or synaptic weights. Likewise, each of the neurons within a network may be understood to have different activation or energy functions; in this regard, such a network may be dubbed a heterogeneous neural network. In some neural networks, at least one of the activation or energy functions may take the form of a sigmoid function, wherein an output thereof may have a range of zero to one, or 0 to 1. In other neural networks, at least one of the activation or energy functions may take the form of a hyperbolic tangent function, wherein an output thereof may have a range of negative one to positive one, or −1 to +1. Further, the training of a neural network according to an identity function results in the redefinition or adjustment of the strengths or weights of such connections between neurons in the various layers of the neural network, in order to provide an output that most closely approximates or associates with the input to the maximum practicable extent.

Artificial neural networks may typically be characterized as either feedforward neural networks or recurrent neural networks, and may be fully or partially connected. In a feedforward neural network, e.g., a convolutional neural network, information specifically flows in one direction from an input layer to an output layer, while in a recurrent neural network, at least one feedback loop returns information regarding the difference between the actual output and the targeted output for training purposes. Additionally, in a fully connected neural network architecture, each of the neurons in one of the layers is connected to all of the neurons in a subsequent layer. By contrast, in a sparsely connected neural network architecture, the number of activations of each of the neurons is limited, such as by a sparsity parameter.

Moreover, the training of a neural network is typically characterized as supervised or unsupervised. In supervised learning, a training set comprises at least one input and at least one target output for the input. Thus, the neural network is trained to identify the target output, to within an acceptable level of error. In unsupervised learning of an identity function, such as that which is typically performed by a sparse autoencoder, target output of the training set is the input, and the neural network is trained to recognize the input as such. Sparse autoencoders employ backpropagation in order to train the autoencoders to recognize an approximation of an identity function for an input, or to otherwise approximate the input. Such backpropagation algorithms may operate according to methods of steepest descent, conjugate gradient methods, or other like methods or techniques, in accordance with the systems and methods of the present disclosure. Those of ordinary skill in the pertinent art would recognize that any algorithm or method may be used to train one or more layers of a neural network. Likewise, any algorithm or method may be used to determine and minimize the error in an output of such a network. Additionally, those of ordinary skill in the pertinent art would further recognize that the various layers of a neural network may be trained collectively, such as in a sparse autoencoder, or individually, such that each output from one hidden layer of the neural network acts as an input to a subsequent hidden layer.

In example embodiments, the machine learning models may be trained using data received from various sensors related to movement and/or location, data related to determined movements and/or locations, data related to correlations between determined movements and/or locations and guide function levels, and/or data related to correlations between determined guide function levels and guide function modifications. By such training, the machine learning models may be trained to determine movements and/or locations of guides and guide devices based on data from various sensors, determine guide function levels based on determined movements and/or locations, and/or determine guide function modifications based on determined guide function levels.

The image recognition algorithms and models may include various types of processing algorithms to determine movement and/or location of a guide and guide device based on imaging data. The image recognition algorithms may include various types of edge detection, object detection, feature detection, or other types of image recognition algorithms. In some example embodiments, the image recognition algorithms may process the imaging data to determine optical flow data related to apparent motion of objects or features in the imaging data, and thereby determine movement and/or location of the guide and guide device. In other example embodiments, the image recognition algorithms may determine that an object represented in the imaging data moves (or does not move) during successive frames of the imaging data, and thereby determine movement and/or location of the guide and guide device. In still other example embodiments, the image recognition or processing algorithms may determine changes in brightness, frequency, wavelength, or other aspects of imaging data or light received by imaging sensors such as photodiodes, and thereby determine movement and/or location of the guide and guide device. In further example embodiments, the image recognition algorithms may recognize one or more objects represented in the imaging data by comparison to stored information of known objects associated with known locations, and thereby determine movement and/or location of the guide and guide device.

The processing algorithms, models, and tools may also include environment models or maps associated with various locations. For example, the environment models may be manually or automatically coded or created, and may also learn, be developed, and/or be refined over time with additional data and inputs, e.g., using machine learning models or other processing algorithms. In example embodiments, the environment models may include data or information associated with one or more locations, such as stored movements or accelerations, stored optical flow data, stored imaging data, stored data associated with recognized objects or features, stored environment data such as altitude, sounds, or weather patterns, or various other stored data associated with one or more locations. In addition, the environment models may include data or information that is associated with particular times of day, times of year, seasons, events, or other time-varying or time-dependent factors. Using such environment models, various data received from one or more sensors of a guide device may be processed and compared with stored data and information of the environment models to identify a movement and/or location of the guide device.

Moreover, various data or information indicating associations between measured data from sensors, determined movements and/or locations of guide devices, various guide function levels, and/or associated guide function modifications may be stored in one or more lookup tables, databases, or other memories. In addition, such stored associations may be continuously refined or updated based on additional data and inputs, e.g., using machine learning models or other processing algorithms. In this manner, one or more processing algorithms may access the stored associations to make determinations and changes related to guide function levels and function modifications based on movements and/or locations of guide devices.

Further, the various processing algorithms, models, and tools may receive and process data from various sensors of the guide device continuously or at one or more frequencies. In addition, one or more thresholds may be associated with the various determinations or outputs of the processing algorithms. The thresholds may comprise a particular number of data samples, particular measured values, particular confidence levels, or other types of thresholds. For example, in order to make a determination with respect to movement and/or location of the guide device, a threshold number of samples or threshold confidence level of the processed data from various sensors may be required. Likewise, in order to make a determination with respect to guide function level and associated guide function modifications, a threshold number of samples or threshold confidence level of the determined movement and/or location may be required. The thresholds associated with determinations of the processing algorithms may ensure that accurate and reliable determinations and changes are made with respect to movements, locations, guide function levels, and/or function modifications, while also maintaining safety and environmental awareness of the guide via prompt and appropriate modifications to the guide device.

Figure 5:
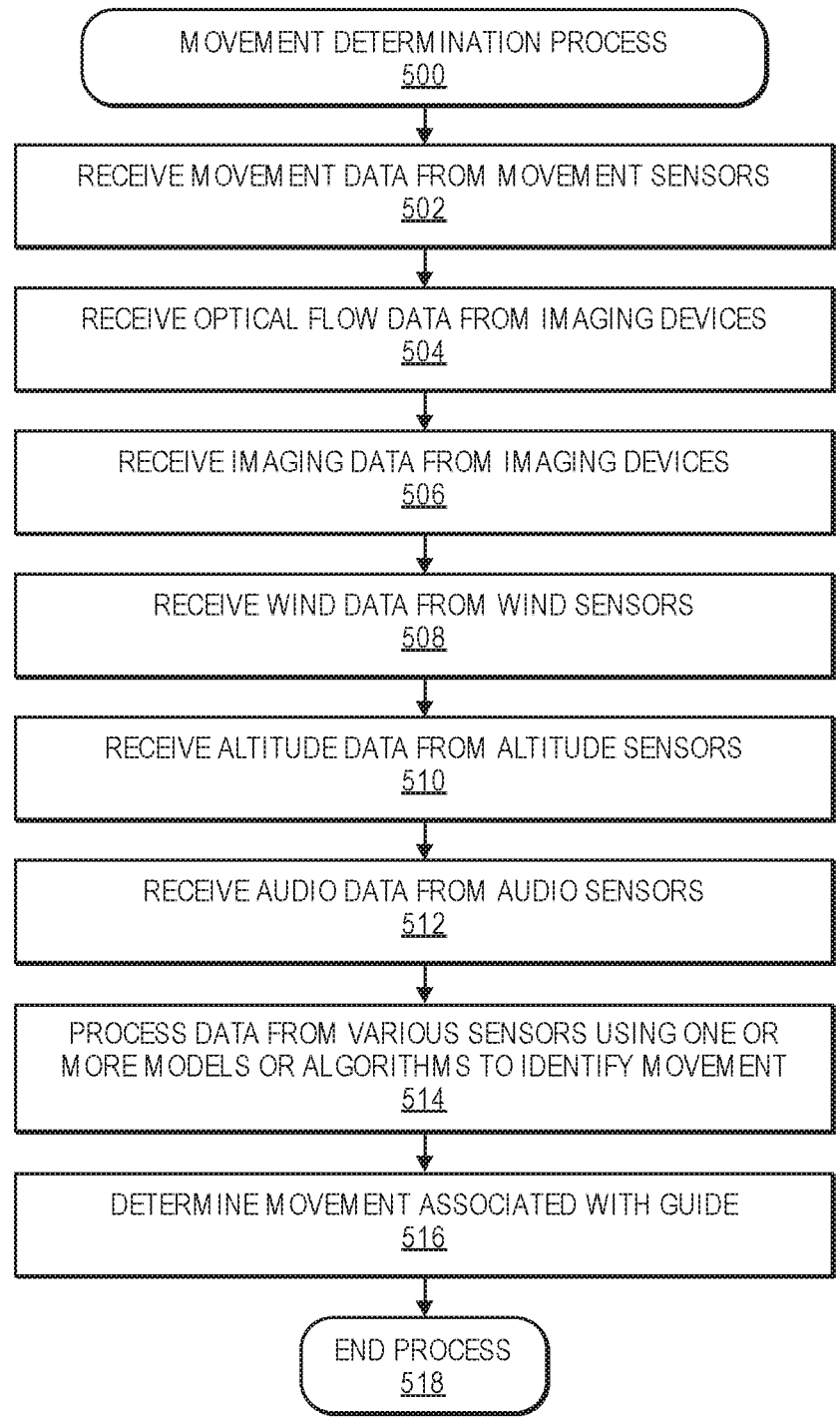
FIG. 5 is a flow diagram illustrating an example movement determination process, according to an implementation.

FIG. 5 is a flow diagram illustrating an example movement determination process 500, according to an implementation.

The process 500 may begin by receiving movement data from movement sensors, as at 502. For example, various movement data associated with movement or acceleration of the guide and guide device may be received from various movement sensors, such as inertial measurement units, accelerometers, gyroscopes, or other movement sensors. In example embodiments, the movement sensors may detect movement or acceleration such as walking, standing, sitting, jumping, running, ascending/descending stairs, hiking, steady movements, erratic movements, or other movements or accelerations of the guide and guide device.

The process 500 may continue by receiving optical flow data from imaging devices, as at 504, and/or by receiving imaging data from imaging devices, as at 506. For example, various imaging data may be received from an imaging component of the guide device, or other imaging sensors, such as optical cameras, infrared cameras, photodiodes, or other types of imaging sensors. In example embodiments, the imaging devices may detect apparent motion of objects in the environment relative to the imaging device, guide, and guide device. In additional example embodiments, the imaging devices may detect over time changes to imaging data, and/or changes to objects or features represented within the imaging data.

The process 500 may proceed by receiving wind data from wind sensors, as at 508, by receiving altitude data from altitude sensors, as at 510, and/or by receiving audio data from audio sensors, as at 512. For example, various environment data may be received from the various sensors, such as wind sensors, pressure or altitude sensors, audio sensors, or other types of environment sensors. In example embodiments, the wind sensors may detect changes in wind or direction of wind that indicate movement, the pressure or altitude sensors may detect changes in altitude that indicate vertical movement, and/or the audio sensors may detect changes to sounds or voices in the environment, including Doppler shifts of sounds such as moving vehicles, that indicate movement.

The process 500 may continue to process the data from various sensors using one or more models or algorithms to identify movement, as at 514. For example, various processing algorithms, such as machine learning models, may be used to process the movement data and identify a movement of the guide device. In addition, various processing algorithms, such as image recognition algorithms and/or machine learning models, may be used to process the imaging data and identify a movement of the guide device. Further various processing algorithms, such as machine learning models, may be used to process the environment data and identify a movement of the guide device.

The process 500 may then proceed to determine movement associated with the guide, as at 516. For example, based on the outputs from the various processing algorithms, a movement of the guide and guide device may be determined. The process 500 may then end, as at 518.

Figure 6:
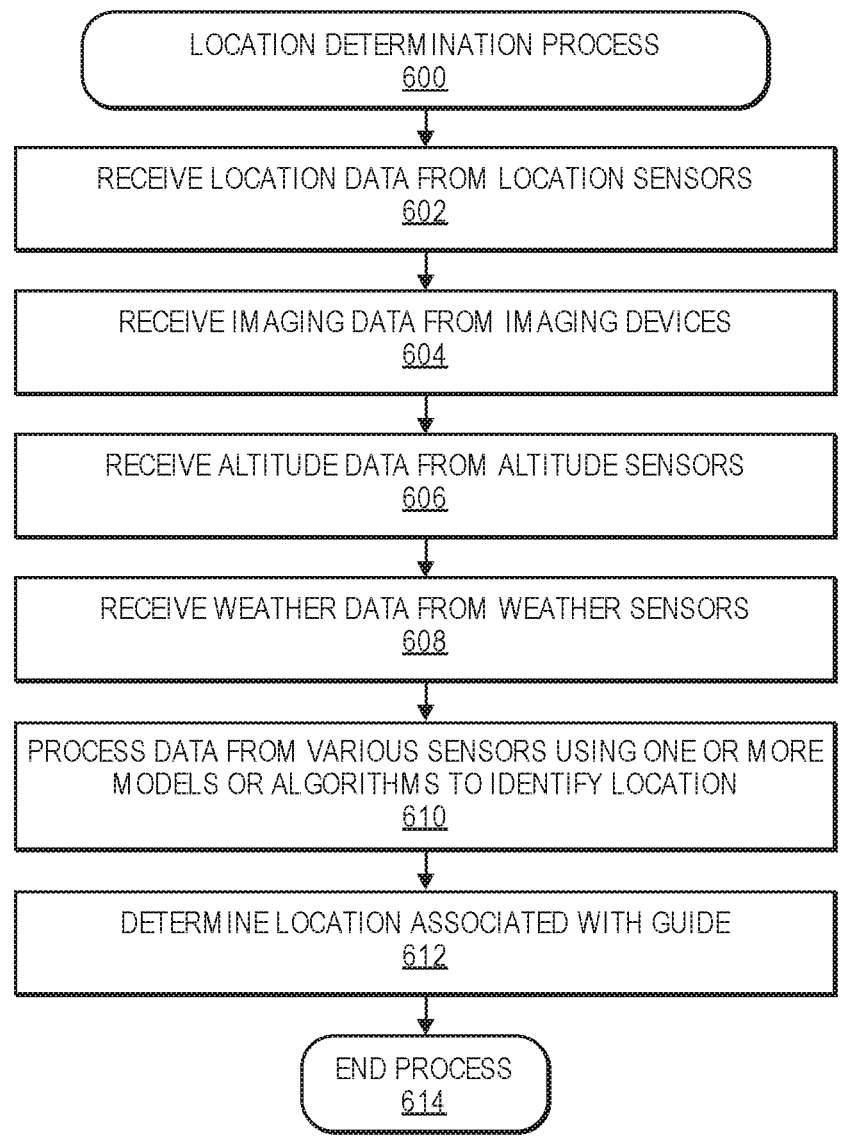
FIG. 6 is a flow diagram illustrating an example location determination process, according to an implementation.

FIG. 6 is a flow diagram illustrating an example location determination process 600, according to an implementation.

The process 600 may begin by receiving location data from location sensors, as at 602. For example, various location data associated with a current location of the guide and guide device may be received from various location sensors, such as GPS sensors, indoor positioning system sensors, cellular signal sensors, other network signal sensors, or other types of location sensors. In example embodiments, the location sensors may receive location or position data from various positioning systems. In other example embodiments, the location sensors may detect network signals that may be used to triangulate location or position of the guide and guide device.

The process 600 may continue by receiving imaging data from imaging devices, as at 604. For example, various imaging data may be received from an imaging component of the guide device, or other imaging sensors, such as optical cameras, infrared cameras, photodiodes, or other types of imaging sensors. In example embodiments, the imaging devices may recognize one or more objects, features, or other aspects represented within imaging data, which may be correlated or associated with a location or position of the guide and guide device.

The process 600 may proceed by receiving altitude data from altitude sensors, as at 606, and/or by receiving weather data from environment sensors, as at 608. For example, various environment data may be received from the various sensors, such as pressure or altitude sensors, audio sensors, or other types of environment sensors. In example embodiments, the pressure or altitude sensors may detect altitudes, or changes thereto, that indicate a location or position of the guide and guide device, the audio sensors may detect sounds or voices in the environment, that indicate a location or position of the guide and guide device, and/or the weather sensors may detect aspects of the weather, such as temperature, humidity, pressure, precipitation, or other aspects, which may be correlated or associated with a location or position of the guide and guide device.

The process 600 may continue to process the data from various sensors using one or more models or algorithms to identify location, as at 610. For example, various processing algorithms, such as machine learning models and/or environment models or maps, may be used to process the location data and identify a current location of the guide device. In addition, various processing algorithms, such as image recognition algorithms, machine learning models and/or environment models or maps, may be used to process the imaging data and identify a current location of the guide device. Further various processing algorithms, such as machine learning models and/or environment models or maps, may be used to process the environment data and identify a current location of the guide device.

The process 600 may then proceed to determine location associated with the guide, as at 612. For example, based on the outputs from the various processing algorithms, a current location of the guide and guide device may be determined. The process 600 may then end, as at 614.

Figure 7:
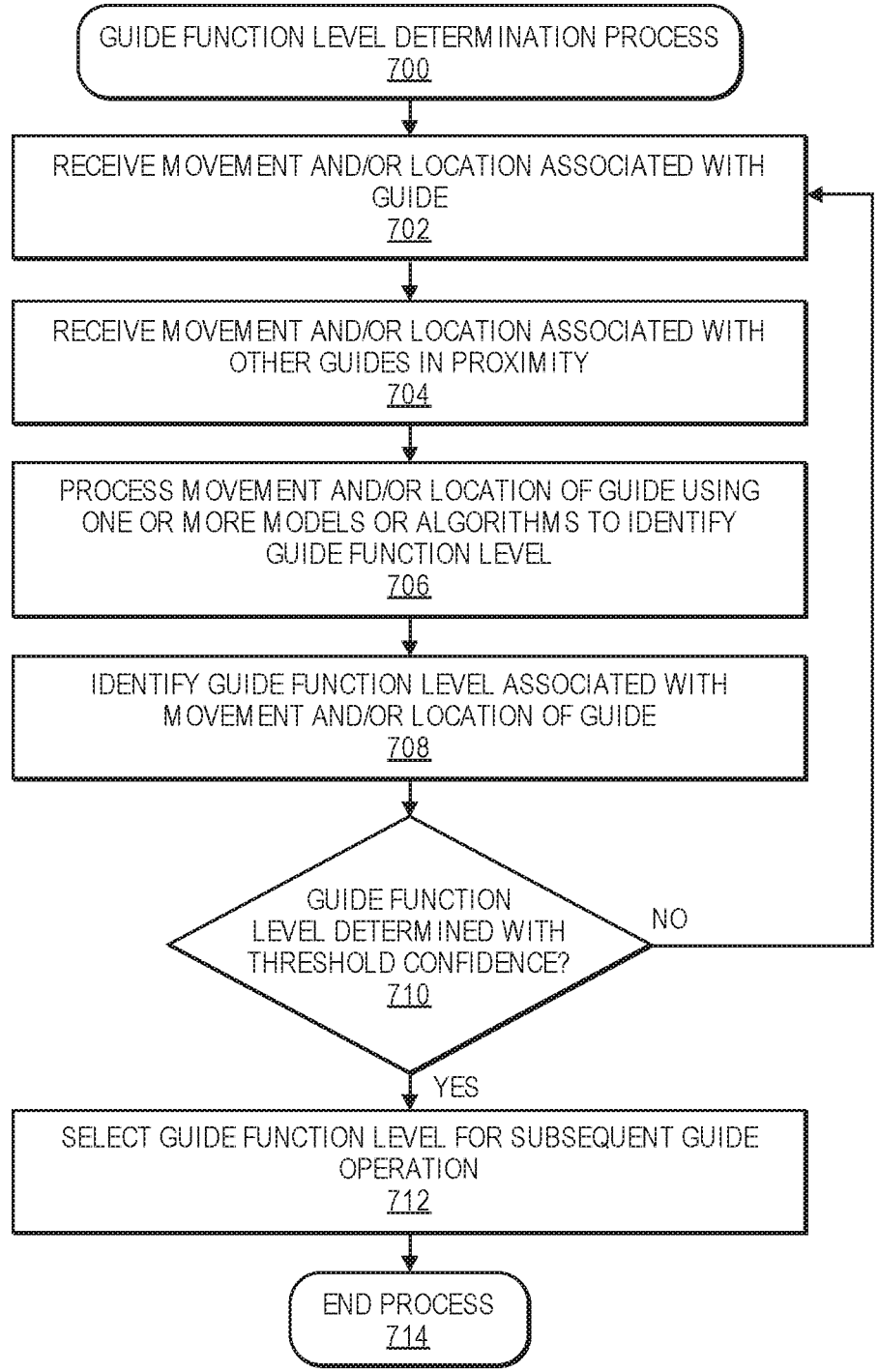
FIG. 7 is a flow diagram illustrating an example guide function level determination process, according to an implementation.

FIG. 7 is a flow diagram illustrating an example guide function level determination process 700, according to an implementation.

The process 700 may begin by receiving movement and/or location associated with a guide, as at 702. For example, the movement and/or location may be determined using the processes 500, 600 described herein with respect to receiving data from various sensors and determining movement and/or location of the guide and guide device.

The process 700 may continue by receiving movement and/or location associated with other guides in proximity, as at 704. For example, movement and/or location of other guides and guide devices in proximity to the guide providing the current experience to the user may also be determined using the processes 500, 600 described herein. The movement and/or location of other guides and guide devices may be used to provide additional data related to surroundings of the guide. Further, the additional data from other guides and guide devices may change a confidence level or other thresholds associated with determined movement and/or location of the guide.

The process 700 may proceed by processing movement and/or location of the guide using one or more models or algorithms to identify a guide function level, as at 706. For example, various processing algorithms, such as machine learning models, environment models or maps, and/or other stored information related to guide function levels, may be used to process the movement and/or location of the guide device and identify a guide function level from a plurality of available guide function levels, as at 708. As described herein, the plurality of available guide function levels may be associated with a range of guide functions that may vary between substantially full manual control by the guide of all functions and/or components of the guide device and substantially full automatic control of all functions and/or components of the guide device, as well as between substantially complete availability and operation of all functions and/or components of the guide device and extremely limited availability and operation of all functions and/or components of the guide device. Moreover, various associations between particular guide function levels and determined movements and/or locations of guide devices may be learned and/or developed over time based on additional data or inputs.

The process 700 may then continue to determine whether the guide function level has been determined with a threshold confidence, as at 710. For example, the threshold confidence may be associated with a number of data samples related to movement and/or location, one or more confidence levels associated with determined movement and/or location, or any other types of thresholds or confidence levels. If the guide function level has not been determined with the threshold confidence, then the process 700 may return to step 702 to receive additional inputs related to movement and/or location associated with the guide, in order to increase the confidence with which the guide function level has been determined.

If the guide function level has been determined with the threshold confidence, then the process 700 may proceed to select the guide function level for subsequence guide operation, as at 712. As described herein, the guide function level may be associated with the movement and/or location of the guide and guide device, which may be learned and/or developed over time based on additional data or inputs. The process 700 may then end, as at 714.

Figure 8:
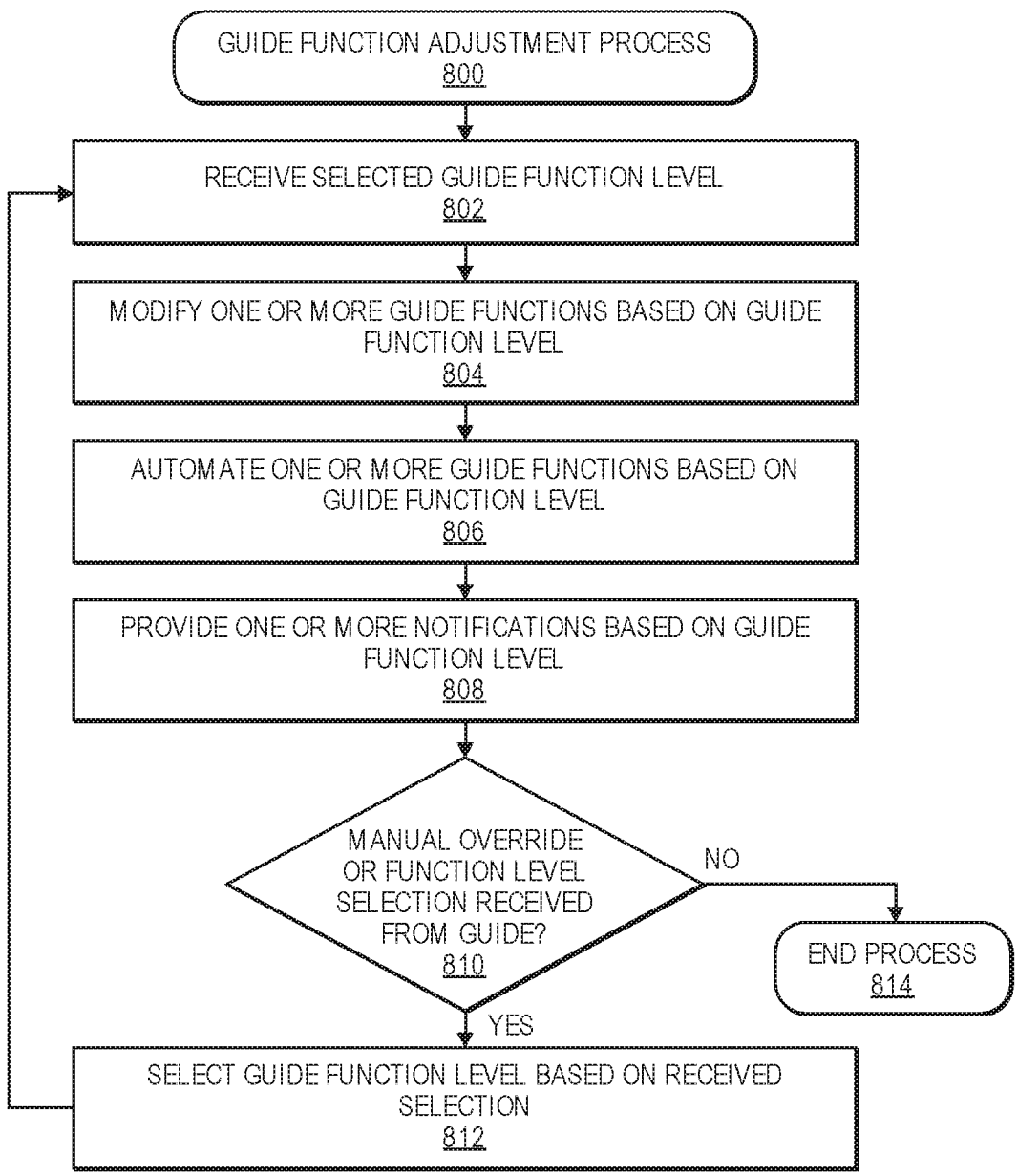
FIG. 8 is a flow diagram illustrating an example guide function adjustment process, according to an implementation.

FIG. 8 is a flow diagram illustrating an example guide function adjustment process 800, according to an implementation.

The process 800 may begin by receiving a selected guide function level, as at 802. For example, the guide function level may be determined using the process 700 described herein with respect to receiving movement and/or location associated with a guide and selecting a guide function level based on the movement and/or location of the guide and guide device. As described herein, various guide functions and their modifications may be associated with the selected guide function level of the guide device, which may be learned and/or developed over time based on additional data or inputs.

The process 800 may proceed by modifying one or more guide functions based on the guide function level, as at 804. For example, various functions of the guide device may be modified, such that one or more functions may be enabled, disabled, suppressed, presented on a user interface, removed from the user interface, or other changes. Other changes to one or more functions and/or user interface elements may also be effected as further described herein.

The process 800 may continue by automating one or more guide functions based on the guide function level, as at 806. For example, various functions of the guide device may be manually controlled, automatically controlled, or at least partially automatically controlled, including control of the imaging component, control of the gimbal, triggering of digital assets or supplemental content, or other functions. Other manual or automatic control of functions or components of the guide device may also be effected as further described herein.

The process 800 may proceed to provide one or more notifications based on the guide function level, as at 808. For example, various notifications, warnings, alerts, or other data and information may be provided or presented to the guide, including information about modified functions, information related to a movement and/or location of the guide, suggestions or recommendations to the guide, or other information. The various notifications may comprise visual, audio, haptic, or other types of notifications or feedback.

The process 800 may continue to determine whether a manual override or function level selection has been received from the guide, as at 810. For example, various options, such as user interface elements or other guide inputs or selections, may be available to the guide such that the guide may alter one or more functions and/or select a particular guide function level. This may allow a guide to enable and/or disable one or more functions of the guide device in a manner different from the determined guide function modifications. Likewise, this may allow a guide to select a guide function level that is different from the guide function level determined based at least in part on the movement and/or location of the guide device. In example embodiments, the manual changes to guide functions and/or manual selection of guide function levels may be processed to refine and/or further train one or more processing algorithms or machine learning models. Further, such refinements may also be stored and/or learned in association with particular guides, particular guide devices, particular movements, particular locations, particular experiences, particular guide function levels, particular guide functions, and/or other aspects or data related to guide function levels and associated functions. For example, by storing and/or learning various aspects related to guide function levels and guide functions, as well as aspects related to movement and/or location, a customized and/or unique set of function levels and function modifications may be associated with each particular guide.

If it is determined that a manual override or function level selection has been received from the guide, then the process 800 may proceed to select the guide function level based on the received manual selection, as at 812. Then, the process 800 may return to step 802 to continue to modify, automate, and/or provide notifications with respect to one or more functions based on the selected guide function level.

If it is determined that a manual override or function level selection has not been received from the guide, then the process 800 may end, as at 814, and the guide device may proceed with subsequent operation using the previously determined guide function level and associated function modifications or changes as described herein.

The various processes 500, 600, 700, 800 may repeat continuously or at particular frequencies or intervals. For example, data from various sensors may be continuously, repeatedly, and/or periodically processed to determine movements and/or locations of the guide and guide device over time. In addition, guide function levels and/or function modifications may be continuously, repeatedly, and/or periodically determined or selected based on determined movements and/or locations of the guide and guide device over time. In this manner, functions available to guides via guide devices may be continuously, repeatedly, and/or periodically changed or updated based on current information associated with movements and/or locations of the guide devices, such that guides may be enabled for providing the best possible experiences to users while also maintaining safety and environmental awareness of the guides.

Further, the various steps of the processes 500, 600, 700, 800 may be performed in different orders, and/or one or more of the steps may be skipped or omitted in example embodiments. For example, in some example embodiments, only movement or only location associated with a guide and guide device may be determined. In addition, only a subset of the various sensors may provide data related to movement and/or location of a guide and guide device. Moreover, only a subset of the various types of modifications to functions of guide devices may be performed, e.g., only user interface elements may be changed, only particular functions may be switched between manual and automatic operation, only notifications may be provided to the guide, or other subsets of changes or modifications.

Figure 9:
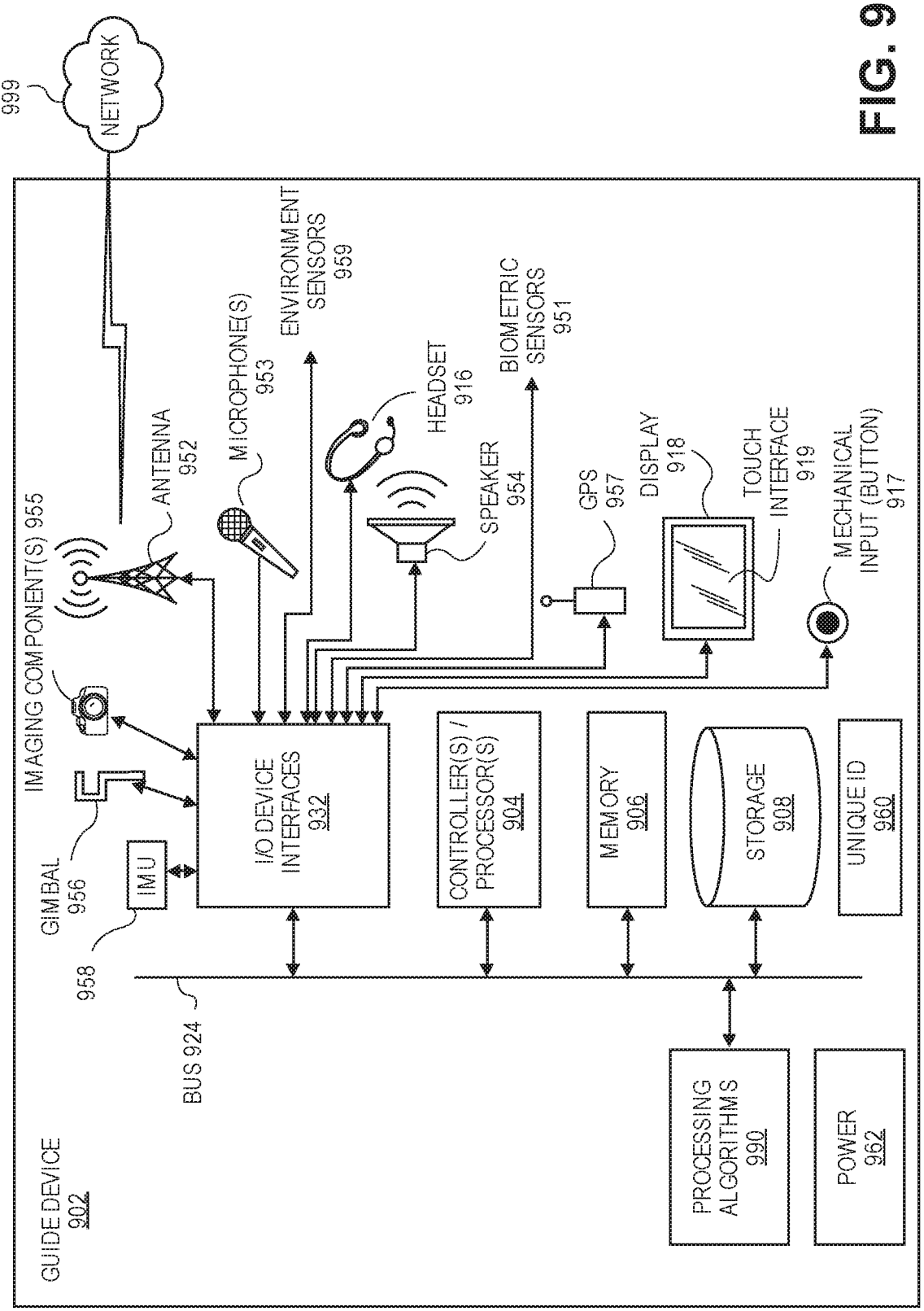
FIG. 9 is a block diagram illustrating an example guide device, according to an implementation.
Figure 10:
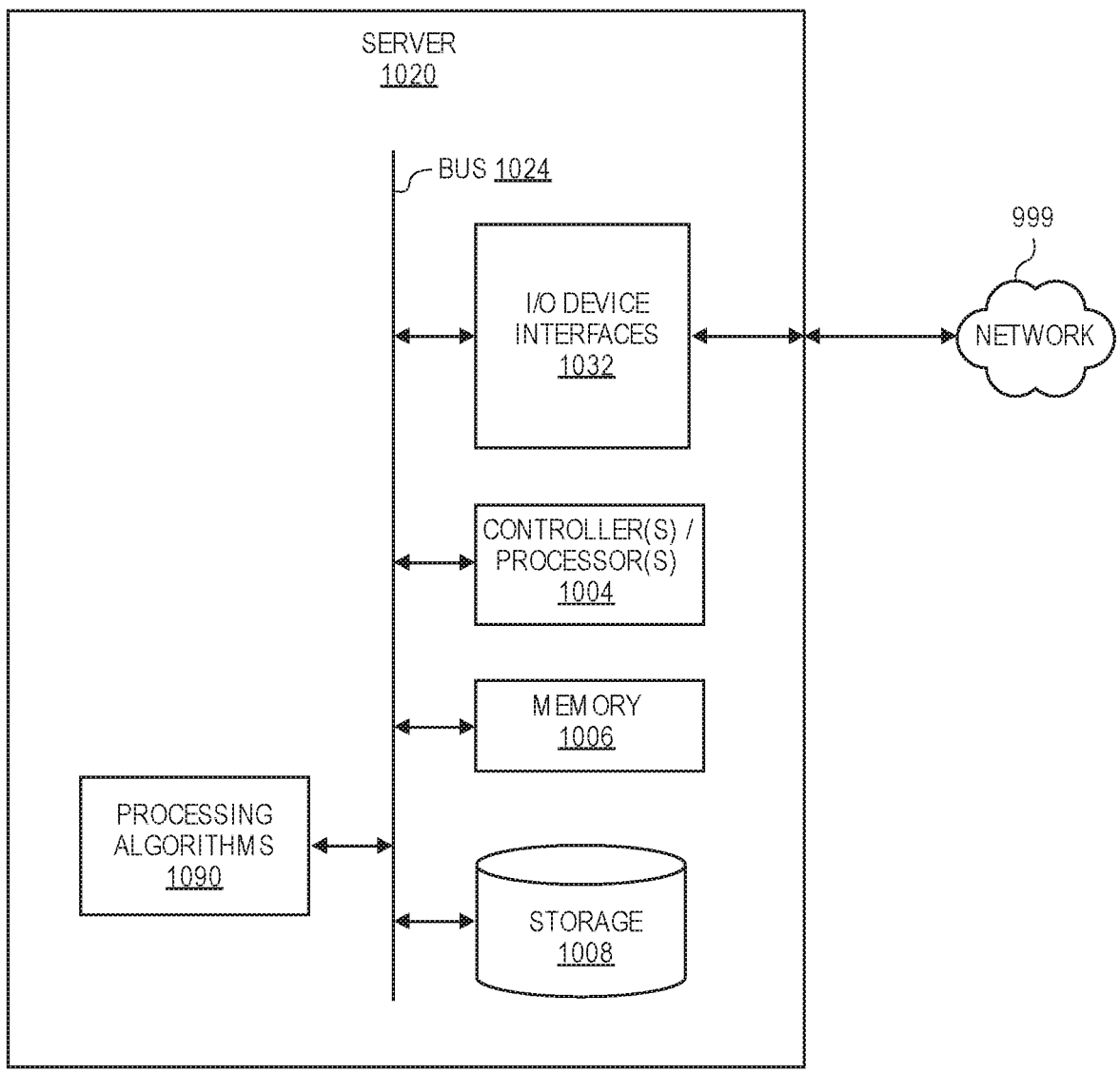
FIG. 10 is a block diagram illustrating example components of a server, according to an implementation.

FIG. 9 is a block diagram illustrating an example guide device 902, according to an implementation. FIG. 10 is a block diagram illustrating example components of a server 1020, according to an implementation, that may assist with processing data from sensors, determining movements or locations of guide devices, determining function levels for guide devices, modifying available functions of guide devices, and other processes described herein. Multiple such servers 1020 may be included in the system, such as one server(s) 1020 for processing data from sensors and determining movements or locations, one server(s) for determining function levels and associated available functions for guide devices, etc. In operation, each of these devices (or groups of devices) may include computer-readable and computer-executable instructions that reside on the respective device (902/1020), as will be discussed further herein.

Each of these devices (902/1020) may include one or more controllers/processors (904/1004), that may each include a central processing unit (CPU) for processing data and computer-readable instructions, and a memory (906/1006) for storing data and instructions of the respective device. In some example embodiments, the controllers/processors (904/1004) may comprise one or more graphics processing units (GPU) that may be configured to accelerate various processing algorithms, such as machine learning models and algorithms, and the one or more GPUs may be used in place of or in combination with other types of processing units to perform the processes described herein. The memories (906/1006) may individually include volatile random access memory (RAM), non-volatile read only memory (ROM), non-volatile magnetoresistive (MRAM) and/or other types of memory. Each device may also include a data storage component (908/1008), for storing data and controller/processor-executable instructions. Each data storage component may individually include one or more non-volatile storage types such as magnetic storage, optical storage, solid-state storage, etc. Each device may also be connected to removable or external non-volatile memory and/or storage (such as a removable memory card, memory key drive, networked storage, etc.) through respective input/output device interfaces (932/1032).

Computer instructions for operating each device (902/1020) and its various components may be executed by the respective device's controller(s)/processor(s) (904/1004), using the memory (906/1006) as temporary "working" storage at runtime. A device's computer instructions may be stored in a non-transitory manner in non-volatile memory (906/1006), storage (908/1008), or an external device(s). Alternatively, some or all of the executable instructions may be embedded in hardware or firmware on the respective device in addition to or instead of software.

Each device (902/1020) includes input/output device interfaces (932/1032). A variety of components may be connected through the input/output device interfaces, as further discussed herein. Additionally, each device (902/1020) may include an address/data bus (924/1024) for conveying data among components of the respective device. Each component within a device (902/1020) may also be directly connected to other components in addition to (or instead of) being connected to other components across the bus (924/1024). Further, any of the various sensors described herein as part of the guide device 902 of FIG. 9 may also be included as part of the server 1020 and/or connected to the server 1020 via the input/output device interface 1032 and/or network 999. In this manner, various of the movement sensors, imaging sensors, location sensors, environment sensors, audio sensors, or other sensors described herein may detect aspects indicating movement and/or location of one or more guides in proximity to the sensors, and this additional data received from various sensors external to any guide devices may additionally be used to determine movement and/or location of one or more guide devices, as well as determine guide function levels and/or function modifications based on the determined movement and/or location.

Referring to the guide device 902 of FIG. 9, the device 902 may include a display 918, which may comprise a touch interface 919. In example embodiments, the display 918 may be associated with one or more components of the guide device. For example, the display may be attached to or integral with the imaging component 955, the gimbal 956, or any other component of the guide device. In addition, the display 918 may generally be within a field of view of the guide using the guide device, such that video data captured by the imaging component 955 and one or more functions available via the guide device may be presented to and viewable by the guide.

In alternative embodiments, the device 902 may be "headless" and may primarily rely on spoken commands and/or mechanical inputs (e.g. buttons) for input. For example, as a way of indicating by a guide that a person or other object within a field of view of the imaging component of the guide device 902 is speaking, the guide may provide an indication through a mechanical input 917, such as a mechanical button. As another example, to provide feedback to the guide that a user is interacting with video data being presented to the user or providing control instructions for the imaging component 955, audible feedback may be output through a speaker 954 and/or through the headset 916 that may be worn by the guide and include a speaker and microphone. Further, feedback may also be provided to the guide via other devices, such as other visual, audio, or haptic feedback devices that may be incorporated into one or more other components of the guide device 902.

The device 902 also includes an imaging component 955, such as a digital video camera, optical imaging sensor, thermal imaging sensor, or other imaging sensor, which may be mounted to the guide, mounted on a gimbal 956 that is held by or attached to the guide, etc. The gimbal 956 may be coupled to the input/output device interface 932 and be configured to receive commands from a user that cause the gimbal to rotate or otherwise change the orientation of the field of view of the imaging component 955. Likewise, the imaging component 955 may receive through the input/output interface 932 commands to generate digital images, alter the zoom of the imaging component 955, etc. Likewise, the imaging component 955 provides video data and/or generated digital images through the input/output interface 932 for transmission to the user device, the display 918 of the guide device, and/or the guide function adjustment service of the remote computing resources 101, as discussed herein. As described herein, the imaging data or video data captured by the imaging component 955 may be processed to determine a movement and/or location of the guide and guide device. In general, the input/output interfaces 932 between the gimbal 956 and the imaging component 955 provide a user at any location that is communicating with the guide and the guide device 902 the ability to control the field of view of the imaging component 955 and selectively determine the content of the destination location presented to the user.

The guide device 902 may also include input/output device interfaces 932 that connect to a variety of other components such as an audio output component, such as a speaker 954, a wired headset or a wireless headset 916, and/or other components capable of outputting audio. The audio capture component may be, for example, a microphone 953 or array of microphones, a wired headset or a wireless headset, etc. The microphone 953 may be configured to capture audio, such as sounds within the destination location and/or speech of other people or objects within the destination location. If an array of microphones is included, approximate distance and direction to a sound's point of origin may be determined using, for example, acoustic localization based on time and amplitude differences between sounds captured by different microphones of the array. Such direction and distance information may be used to determine if a person or object speaking is within a field of view of the imaging component to determine whether presented audio data and video data at the user device needs to be synchronized.

The guide device also includes one or more antennas 952 that connect to one or more networks 999 via a wireless local area network (WLAN) (such as Wi-Fi) radio, Bluetooth, and/or wireless network radio, such as a radio capable of communication with a wireless communication network such as a Long Term Evolution (LTE) network, WiMAX network, 3G network, cellular network, etc. Through the network(s) 999, audio data, video data, data from various sensors, guide function adjustment information, etc. may be transmitted between the guide device 902, the guide function adjustment service of the remote computing resources 101, and/or the user device for presentation by the user device to a user that is communicating with the guide and controlling components of the guide device 902 and/or for presentation by the guide device to a guide providing the experience to the user. As described herein, cellular or other network signal information may be detected by the antennas 952 and processed to determine a movement and/or location of the guide and guide device.

The guide device 902 may also include one or more location sensors 957, such as a GPS sensor, an indoor positioning system sensor that may determine location based on Wi-Fi signals, or other location based component or sensor. The location sensors 957 may be associated with one or more components of the guide device. For example, the location sensors 957 may be attached to or integral with the processor 904, the imaging component 955, the gimbal 956, or any other component of the guide device. As described herein, location data received by the location sensors 957 may be processed to determine a current location of the guide and guide device.

The guide device may also include one or more movement sensors 958, such as inertial measurement units (IMU), accelerometers, gyroscopes, or other movement or acceleration sensors. As is known in the art, an IMU may include an accelerometer, a gyroscope, and/or a compass and provide movement, position, and/or orientation information based on the accelerometer, gyroscope and/or compass. In some implementations, a movement sensor 958 may be included in the gimbal 956 and provide information indicating a movement, position, and/or orientation of the imaging component 955 mounted to the gimbal. As another example, a movement sensor 958 may be included on the imaging component 955 and provide information indicating a movement, position, and/or orientation of the imaging component 955. In still other examples, a movement sensor 958 may be included on the processor 904, a backpack, bag, or wearable component or device that comprises or houses one or more components of the guide device, the guide themselves, and/or any other component of the guide device, and provide information indicating a movement, position, and/or orientation of the guide and guide device. As described herein, movement data received by the movement sensor 958 may be processed to determine a movement and/or location of the guide and guide device.

The guide device may also include one or more environment sensors 959, such as wind sensors, pressure sensors, altitude sensors, weather sensors, audio sensors, or other types of sensors. The environment sensors 959 may be associated with one or more components of the guide device. In some implementations, a wind sensor may detect a change in wind due to a change in orientation (e.g., a guide turning toward or away from a direction of wind) or a change in wind due to a different rate of travel of the guide. In other implementations, a pressure or altitude sensor may detect an altitude, or a change thereof, of the guide. In still other implementations, a weather sensor may detect various aspects of the environment, such as temperature, humidity, pressure, precipitation, or other aspects related to weather. In further implementations, an audio sensor may detect sounds or voices in the environment, including sounds that may be approaching closer to or retreating away from the guide (e.g., based on Doppler shift of sound waves). As described herein, environment data received by the environment sensors 959 may be processed to determine a movement and/or location of the guide and guide device.

The guide device may also include one or more biometric sensors 951, such as pulse detection sensors, temperature sensors, contact sensors, or other sensors to detect aspects related to the guide. The biometric sensors 951 may be associated with one or more components of the guide device, particularly portions of the guide device that may contact or be in proximity to the guide, such as the gimbal 956, the imaging component 955, the headset 916 or other wearable component, a backpack or bag carried or worn by the guide, or any other component of the guide device. In some implementations, a pulse, body temperature, perspiration, grip pressure, or other aspects related to the guide may be detected by the biometric sensors 951 and processed to determine stress, fatigue, or other physical or emotional states of the guide. Such determinations related to physical or emotional states of the guide may also be taken into account when adjusting function levels, and associated available functions thereof, for guide devices and guides, in combination with determinations related to a movement and/or location of the guide and guide device. Moreover, such determinations related to physical or emotional states of the guide may also be received and processed as indicators of movement and/or location of the guide and guide device. For example, an increased pulse rate or elevated body temperature may be indicators of running, ascending/descending several flights of stairs, and/or hiking along uneven terrain.

The guide device may also include one or more power sources 962. For example, the power source may comprise a battery, a wireless power connection, a wired power connection, or other power source configured to provide power to one or more components of the guide device, including the processor 904, imaging component 955, gimbal 956, and various of the input/output devices and/or sensors.

In some implementations, the guide device 902 and/or the server 1020 may include one or more processing algorithms, models, or tools 990/1090, including machine learning models or algorithms, image recognition algorithms or models, environment maps or models, or other processing algorithms described herein, that are configured to process data received from various sensors of the guide device 902. As discussed herein, the processing algorithms 990/1090 may process the received data to determine a movement and/or location of a guide and guide device, to determine a guide function level for the guide device based at least in part on the determined movement and/or location, and/or to modify one or more functions of the guide device based at least in part on the determined guide function level.

Multiple guide devices may be employed in a single system and different users may connect with, communicate with and control different guide devices. As such, each guide device may also include a unique identifier 960. The unique identifier may be any form of unique identification and may be included in video data, audio data, sensor data, or other data that is transmitted from the guide device. Likewise, a user device and/or the remote computing resources may utilize the unique identifier to enable communication and/or control with the guide device. In such a multi-device system, each of the guide devices may include the same or different components. The components of the guide device 902 and the server 1020, as illustrated in FIGS. 9 and 10, are exemplary, and should not be considered limiting to the implementations discussed herein.

The concepts disclosed herein may be applied within a number of different devices and computer systems, including, for example, general-purpose computing systems, video processing systems, and distributed computing environments.

The described aspects of the present disclosure are meant to be illustrative. They were chosen to explain the principles and application of the disclosure and are not intended to be exhaustive or to limit the disclosure. Many modifications and variations of the disclosed aspects may be apparent to those of skill in the art. Persons having ordinary skill in the field of computers, communications, sensors, data and video processing, and computing device functionality should recognize that components and process steps described herein may be interchangeable with other components or steps, or combinations of components or steps, and still achieve the benefits and advantages of the present disclosure. Moreover, it should be apparent to one skilled in the art that the disclosure may be practiced without some or all of the specific details and steps disclosed herein.

Aspects of the disclosed system may be implemented as a computer method or as an article of manufacture such as a memory device or non-transitory computer readable storage medium. The computer readable storage medium may be readable by a computer and may comprise instructions for causing a computer or other device to perform processes described in the present disclosure. The computer readable storage media may be implemented by a volatile computer memory, non-volatile computer memory, hard drive, solid-state memory, flash drive, removable disk and/or other media.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Language of degree used herein, such as the terms "about," "approximately," "generally," "near," "nearly" or "substantially" as used herein, represent a value, amount, or characteristic close to the stated value, amount, or characteristic that still performs a desired function or achieves a desired result. For example, the terms "about," "approximately," "generally," "near," "nearly" or "substantially" may refer to an amount that is within less than 10% of, within less than 5% of, within less than 1% of, within less than 0.1% of, and within less than 0.01% of the stated amount.

Although the invention has been described and illustrated with respect to illustrative implementations thereof, the foregoing and various other additions and omissions may be made therein and thereto without departing from the spirit and scope of the present disclosure.

What is claimed is:

1. A computer-implemented method to adjust functionality of a guide computing device, comprising:
receiving, from a movement sensor associated with the guide computing device, movement data;
receiving, from an imaging sensor associated with the guide computing device, imaging data;
receiving, from a location sensor associated with the guide computing device, location data;
processing the movement data, the imaging data, and the location data to identify a movement associated with the guide computing device, wherein the movement comprises an acceleration;
identifying, from a plurality of function levels, a function level for the guide computing device based at least in part on the movement, wherein each of the plurality of function levels comprises different available functions of the guide computing device based at least in part on the movement;
selecting the identified function level for operation of the guide computing device; and
modifying at least one function of the guide computing device based at least in part on the identified function level;
wherein modifying the at least one function of the guide computing device based at least in part on the identified function level further comprises at least one of:
enabling the at least one function of the guide computing device;
disabling the at least one function of the guide computing device;
allowing manual control of the at least one function of the guide computing device; or
automating the at least one function of the guide computing device.

2. The computer-implemented method of claim 1, wherein the movement data comprises at least one of horizontal, vertical, rotational, or acceleration movement data.

3. The computer-implemented method of claim 1, wherein the imaging data comprises at least one of optical flow data, one or more images, or video data.

4. The computer-implemented method of claim 1, wherein the location data comprises at least one of global positioning system data, indoor positioning system data, or cellular signal data.

5. A computer-implemented method, comprising:
receiving, from at least one sensor associated with a computing device, data indicating a movement associated with the computing device;
processing the data to identify the movement associated with the computing device, wherein the movement comprises an acceleration;
selecting, from a plurality of function levels, a function level for the computing device based at least in part on the movement, wherein each of the plurality of function levels comprises different available functions of the computing device based at least in part on the movement; and
modifying at least one function of the computing device based at least in part on the selected function level;
wherein modifying the at least one function of the computing device based at least in part on the selected function level further comprises at least one of:
enabling the at least one function of the computing device;
disabling the at least one function of the computing device;
allowing manual control of the at least one function of the computing device; or
automating the at least one function of the computing device.

6. The computer-implemented method of claim 5, wherein the at least one sensor comprises at least one of an inertial measurement unit, an accelerometer, or a gyroscope; and
wherein processing the data to identify the movement associated with the computing device further comprises:
identifying an acceleration based on movement data from the at least one of the inertial measurement unit, the accelerometer, or the gyroscope;
comparing the identified acceleration with known accelerations; and
identifying the movement associated with the computing device based at least in part on the comparison.

7. The computer-implemented method of claim 5, wherein the at least one sensor comprises an imaging sensor; and
wherein processing the data to identify the movement associated with the computing device further comprises:
determining an optical flow based on imaging data from the imaging sensor; and
identifying the movement associated with the computing device based at least in part on the optical flow.

8. The computer-implemented method of claim 5, wherein the at least one sensor comprises an imaging sensor; and
wherein processing the data to identify the movement associated with the computing device further comprises:
identifying an object represented in a first image from the imaging sensor;
identifying the object represented in a second image from the imaging sensor;
determining a movement of the object based on the first and second images; and
identifying the movement associated with the computing device based at least in part on the determined movement of the object.

9. The computer-implemented method of claim 5, wherein the at least one sensor comprises an environment sensor; and
wherein processing the data to identify the movement associated with the computing device further comprises:
identifying at least one of a change in wind or a change in altitude based on environment data from the environment sensor; and
identifying the movement associated with the computing device based at least in part on the identified change in wind or change in altitude.

10. The computer-implemented method of claim 5, wherein the at least one sensor comprises at least one of a global positioning system sensor, an indoor positioning system sensor, or a cellular signal sensor; and wherein processing the data to identify the movement associated with the computing device further comprises:
identifying a location based on location data from the at least one of the global positioning system sensor, the indoor positioning system sensor, or the cellular signal sensor;
comparing the identified location with known locations; and
identifying a location associated with the computing device based at least in part on the comparison.

11. The computer-implemented method of claim 5, wherein the at least one sensor comprises an imaging sensor; and
wherein processing the data to identify the movement associated with the computing device further comprises:
recognizing an object represented in an image from the imaging sensor;
identifying a location associated with the recognized object; and
identifying a location associated with the computing device based at least in part on the identified location of the recognized object.

12. The computer-implemented method of claim 5, wherein the at least one sensor comprises an environment sensor; and
wherein processing the data to identify the movement associated with the computing device further comprises:
identifying at least one of a change in altitude or a change in weather based on environment data from the environment sensor; and
identifying a location associated with the computing device based at least in part on the identified change in altitude or change in weather.

13. The computer-implemented method of claim 5, wherein modifying the at least one function of the computing device based at least in part on the selected function level further comprises:
providing a notification associated with the at least one function of the computing device.

14. The computer-implemented method of claim 5, wherein the at least one function comprises at least one of:
transmission of imaging data via the computing device;
receipt of imaging data via the computing device;
transmission of audio data via the computing device;
receipt of audio data via the computing device;
controlling a camera associated with the computing device;
selecting a user interface element via a user interface associated with the computing device;
providing a digital asset to a user via the computing device;
completing a purchase on behalf of a user via the computing device;
communicating with a user via the computing device;
completing a review of a user via the computing device; or
turning on or off the computing device.

15. The computer-implemented method of claim 5, further comprising:
receiving a manual selection of a second function level for the computing device, wherein the second function level is different than the function level selected based at least in part on the movement; and
modifying at least one function of the computing device based at least in part on the selected second function level.

16. An apparatus, comprising:
an imaging device configured to capture an image of an environment;
a user interface configured to display the image and one or more user interface elements;
at least one sensor configured to detect a movement associated with the apparatus; and
a processor in communication with the imaging device, the user interface, and the at least one sensor, the processor configured to at least:
receive, from the at least one sensor, data indicating the movement associated with the apparatus;
process the data to identify the movement associated with the apparatus, wherein the movement comprises an acceleration;
select, from a plurality of function levels, a function level for the apparatus based at least in part on the movement, wherein each of the plurality of function levels comprises different available functions of the apparatus based at least in part on the movement; and
modify at least one function of the apparatus based at least in part on the selected function level;
wherein modifying the at least one function of the apparatus based at least in part on the selected function level further comprises at least one of:
enabling the at least one function of the apparatus:
disabling the at least one function of the apparatus;
allowing manual control of the at least one function of the apparatus: or
automating the at least one function of the apparatus.

17. The apparatus of claim 16, wherein the at least one sensor comprises at least one of an inertial measurement unit, an accelerometer, a gyroscope, an imaging sensor, a global positioning system sensor, an indoor positioning system sensor, a cellular signal sensor, a wind sensor, a pressure sensor, an altitude sensor, an audio sensor, or a weather sensor.

18. The apparatus of claim 16, further comprising:
a gimbal configured to control an orientation of the imaging device; and
wherein the at least one function comprises controlling the orientation of the imaging device.

19. The apparatus of claim 16, wherein the at least one function comprises at least one of availability or operability of the one or more user interface elements displayed via the user interface.

* * * * *